US012729372B2

(12) United States Patent
Gao et al.

(10) Patent No.: US 12,729,372 B2
(45) Date of Patent: Sep. 8, 2026

(54) IMMUNOTHERAPY METHOD OF TARGETED CHEMOKINE AND CYTOKINE DELIVERY BY MESENCHYMAL STEM CELL

(71) Applicant: CHANGEN THERAPEUTICS (SHANGHAI) CO., LTD., Shanghai (CN)

(72) Inventors: Wei Qiang Gao, Shanghai (CN); Bin Ma, Shanghai (CN); Pan Yin, Shanghai (CN)

(73) Assignee: CHANGEN THERAPEUTICS (SHANGHAI) CO., LTD., Shanghai (CN)

( * ) Notice: Subject to any disclaimer, the term of this patent is extended or adjusted under 35 U.S.C. 154(b) by 720 days.

(21) Appl. No.: 18/005,166

(22) PCT Filed: Jul. 16, 2020

(86) PCT No.: PCT/CN2020/102473
§ 371 (c)(1),
(2) Date: Jan. 11, 2023

(87) PCT Pub. No.: WO2022/011651
PCT Pub. Date: Jan. 20, 2022

(65) Prior Publication Data

US 2023/0257713 A1 Aug. 17, 2023

(51) Int. Cl.
*C12N 5/0775* (2010.01)
*A61K 35/28* (2015.01)
*A61P 35/00* (2006.01)
*C07K 14/52* (2006.01)
*C12N 5/10* (2006.01)

(52) U.S. Cl.
CPC ............ *C12N 5/0668* (2013.01); *A61K 35/28* (2013.01); *A61P 35/00* (2018.01); *C07K 14/521* (2013.01); *C12N 5/0665* (2013.01); *C12N 5/10* (2013.01)

(58) Field of Classification Search
CPC .... C12N 5/0668; C12N 5/10; C12N 2510/00; A61K 40/35
See application file for complete search history.

(56) References Cited

U.S. PATENT DOCUMENTS 5,350,674 A 9/1994 Boenisch et al.
5,399,346 A 3/1995 Anderson et al.
5,580,859 A 12/1996 Felgner et al.
5,585,362 A 12/1996 Wilson et al.
5,589,466 A 12/1996 Felgner et al.
6,326,193 B1 12/2001 Liu et al.
2018/0105797 A1 4/2018 Brodie et al.
2018/0256742 A1* 9/2018 Poznansky ............ A61K 40/11
2020/0171093 A1 6/2020 Lu et al.

FOREIGN PATENT DOCUMENTS

CN 107916253 A 4/2018
CN 110996975 A 4/2020
CN 111139222 A 5/2020
JP 2017531425 A 10/2017
JP 2019513367 A 5/2019
JP 2020500008 A 1/2020
JP 2020516654 A 6/2020
WO 0129058 A1 4/2001
WO 0196584 A2 12/2001
WO 2016026854 A2 2/2016
WO WO-2018191619 A1 * 10/2018 ............. A61P 35/00
WO 2019073973 A1 4/2019
WO 2020081869 A1 4/2020

OTHER PUBLICATIONS

Zhang, Haiwang et al.; "Research progress of mesenchymal stem cell carrier gene therapy formalignant glioma"; Journal of International Neurology and Neurosurgery; vol. 40, No. 3; Dec. 31, 2013; pp. 251-254.
Kim, Seong Muk et al.; "Gene Therapy Using TRAIL-Secreting Human Umbilical Cord Blood-Derived Mesenchymal Stem Cells against Intracranial Glioma"; Cancer Research; vol. 68, No. 23; Dec. 1, 2008; pp. 9614-9623.
Kopru, Cagla Zubeyde et al., "Dual Effect of Glucocorticoid-InducedTumor Necrosis Factor-Related Receptor Ligand Carrying Mesenchymal Stromal Cells on Small Cell Lung Cancer: A Preliminary in vitro Study", Cytotherapy, Jul. 2018, vol. 20. No. 7, pp. 1-11.

* cited by examiner

*Primary Examiner* — Taeyoon Kim
(74) *Attorney, Agent, or Firm* — NKL Law; Bin Lu; Allen Xue

(57) ABSTRACT

An immunotherapy method of targeted chemokine and cytokine delivery by a mesenchymal stem cell that expresses an immunostimulatory factor. The immunostimulatory factor is selected from the following group: CCL3, CCL19, CCL21, XCL1, CXCL9, OX40L, 4-1BBL, GITRL, CD40L, or a combination thereof. At a tumor site, the mesenchymal stem cell specifically attracts and activates an immune cell that kills tumor tissue, and the mesenchymal stem cell has a synergistic effect with chemokines and/or cytokines, having an immunotherapeutic effect with higher efficiency and few side effects, and a significantly enhanced ability to kill tumor tissue, especially colorectal cancer cells.

10 Claims, 16 Drawing Sheets

IMMUNOTHERAPY METHOD OF TARGETED CHEMOKINE AND CYTOKINE DELIVERY BY MESENCHYMAL STEM CELL

TECHNICAL FIELD

The present invention relates to the field of biotechnology, in particular to an immunotherapy of targeted chemokine and cytokine delivery by mesenchymal stem cells.

BACKGROUND

The rapid development of immunotherapy has shed new fight to cancers, especially chimeric antigen receptor T cell immunotherapy (CAR-T) and immunomodulatory checkpoint blockade which are two relatively cutting-edge cancer immunotherapies. CAR-T cell therapy has shown certain efficacy in some types of cancer, but it has also encountered bottlenecks such as low reaching efficiency to the solid tumor and short action time of T cells, small number of immune cells in the tumor site, side effects caused by systemic medication and the like. The use of antibodies targeting the T cell inhibitory receptors PD-1 or CTLA-4 can produce very significant anti-tumor effects. However, the therapeutic effect of antibody is often limited by many factors, such as the low infiltration and loss of activity of T cells in solid tumors. In addition, systemic use of immunotherapy drugs such as interferon of α, interleukin 2, or PD-1 antibodies may cause serious side effects.

Therefore, there is an urgent need in the art for an immunotherapy that can specifically target tumor cells.

SUMMARY OF THE INVENTION

The purpose of the present invention is to provide an immunotherapy that can specifically target tumor cells.

Another purpose of the present invention is to provide an immunotherapy of targeted chemokine and cytokine delivery by mesenchymal stem cells.

In the first aspect of the present, it provides a mesenchymal stem cell expressing an immunostimulatory factor, wherein the immunostimulatory factor is selected from the group consisting of: CCL3, CCL19, CCL21, XCL1, CXCL9, OX40L, 4-1BBL, GITRL, CD40L, and a combination thereof.

In another preferred embodiment, the mesenchymal stem cell comprises an exogenous nucleic acid molecule comprising a nucleic acid sequence encoding an immunostimulatory factor selected from the following group: CXCL9, OX40L, CCL3, CCL19, CCL21, XCL1, CXCL9, OX40L, 4-1BBL, GITRL, CD40L, and a combination thereof.

In another preferred embodiment, the exogenous nucleic acid molecule further comprises a promoter or a promoter/enhancer combination, wherein the nucleic acid sequence encoding the immunostimulatory factor is operatively connected to the promoter or promoter/enhancer combination.

In another preferred embodiment, the promoter is a constitutive promoter or an inducible promoter, preferably a constitutive promoter.

In another preferred embodiment, the immunostimulatory factor comprises at least one chemokine, wherein the chemokine includes: CCL3, CCL19, CCL21, XCL1, CXCL9, and a combination thereof.

In another preferred embodiment, the immunostimulatory factor comprises at least one cytokine, wherein the cytokine includes: OX40L, 4-1BBL, GITRL, CD40L, and a combination thereof.

In another preferred embodiment, the immunostimulatory factor comprises at least one chemokine and at least one cytokine, wherein the chemokine includes: CCL3, CCL19, CCL21, XCL1, CXCL9, and a combination thereof, and the cytokine includes: OX40L, 4-1BBL, GITRL, CD40L, and a combination thereof.

In another preferred embodiment, the immunostimulatory factor is a combination of one or two of CCL3, CCL19, CCL21 and XCL1, with CD40L.

In another preferred embodiment, the immunostimulatory factor is a combination of one or two of OX40L, 4-1BBL, and GITRL, with CXCL9.

In another preferred embodiment, the immunostimulatory factor is CXCL9 and/or OX40L.

In another preferred embodiment, the exogenous nucleic acid molecule comprises a first expression cassette and/or a second expression cassette, wherein the first expression cassette comprises a nucleic acid sequence encoding a chemokine, and the second expression cassette comprises a nucleic acid sequence encoding a cytokine, wherein the chemokine includes: CCL3, CCL19, CCL21, XCL1, CXCL9, and a combination thereof, and the cytokine includes: OX40L, 4-1BBL, GITRL, CD40L, and a combination thereof.

In another preferred embodiment, the exogenous nucleic acid molecule comprises a first expression cassette and a second expression cassette, wherein the first expression cassette comprises a nucleic acid sequence encoding CXCL9, and the second expression cassette comprises a nucleic acid sequence encoding OX40L.

In another preferred embodiment, the first expression cassette and the second expression cassette are independent or connected.

In another preferred embodiment, the first expression cassette and the second expression cassette further include a promoter and/or a terminator, respectively.

In another preferred embodiment, the first expression cassette and the second expression cassette are the same expression cassette, wherein the expression cassette comprises a promoter, a nucleic acid sequence encoding a chemokine and a nucleic acid sequence encoding a cytokine.

In another preferred embodiment, the first expression cassette and the second expression cassette are on a vector or integrated into a chromosome of the mesenchymal stem cell.

In another preferred embodiment, the first expression cassette and the second expression cassette are independent or connected.

In another preferred embodiment, the first expression cassette and the second expression cassette are in the same or different vectors.

In another preferred embodiment, the first expression cassette and the second expression cassette are in the same vector.

In another preferred embodiment, the vector is selected from the group consisting of DNA, RNA, plasmid, lentiviral vector, adenoviral vector, retroviral vector, transposon, other gene transfer system, and a combination thereof.

In another preferred embodiment, the mesenchymal stem cell includes: an adipose mesenchymal stem cell, an umbilical cord mesenchymal stem cell, and a combination thereof.

In another preferred embodiment, the mesenchymal stem cell is ex vivo.

In another preferred embodiment, the mesenchymal stem cell is autologous or allogeneic.

In the second aspect of the present invention, it provides a method for preparing the mesenchymal stem cell according to the first aspect of the present invention, comprising the following steps:

(1) providing a mesenchymal stem cell to be modified; and (2) introducing an exogenous nucleic acid containing a nucleic acid sequence that encodes an immunostimulatory factor into the mesenchymal stem cell to be modified, thereby obtaining the mesenchymal stem cell according to the first aspect of the present invention;

wherein the immunostimulatory factor is selected from the group consisting of: CCL3, CCL19, CCL21, XCL1, CXCL9, OX40L, 4-1BBL, GITRL, CD40L, and a combination thereof.

In the third aspect of the present invention, it provides a preparation comprising the mesenchymal stem cell according to the first aspect of the present invention, and a pharmaceutically acceptable carrier, diluent or excipient.

In another preferred embodiment, the preparation is a liquid preparation.

In another preferred embodiment, the dosage form of the preparation includes an injection.

In another preferred embodiment, the concentration of the mesenchymal stem cell in the preparation is $1\times10^3$-$1\times10^8$ cells/ml, preferably $1\times10^4$-$1\times10^7$ cells/ml.

In the fourth aspect of the present invention, it provides a use of the mesenchymal stem cell according to the first aspect of the present invention, for preparing a drug or preparation for preventing and/or treating a cancer or tumor In another preferred embodiment, the tumor is selected from the group consisting of a hematological tumor, a solid tumor, and a combination thereof. Preferably the tumor is a solid tumor.

In another preferred embodiment, the hematological tumor is selected from the group consisting of acute myeloid leukemia (AML), multiple myeloma (MM), chronic lymphocytic leukemia (CLL), acute lymphocytic leukemia (ALL), diffuse large B cell lymphoma (DLBCL), and a combination thereof.

In another preferred embodiment, the solid tumor is selected from the group consisting of gastric cancer, gastric cancer peritoneal metastasis, liver cancer, leukemia, kidney tumor, lung cancer, small intestinal cancer, bone cancer, prostate cancer, colorectal cancer, breast cancer, colorectal cancer, cervical cancer, ovarian cancer, lymphoma, nasopharyngeal cancer, adrenal tumor, bladder tumor, non-small cell lung cancer (NSCLC), brain glioma, endometrial cancer, lung squamous cell carcinoma, anal cancer, head and neck cancer and a combination thereof.

In another preferred embodiment, the solid tumor is a colorectal cancer.

In another preferred embodiment, the tumor includes recurrent, metastatic tumors.

In another preferred embodiment, the tumor includes MHC-I-deficient tumors.

In the fifth aspect of the present invention, it provides a medicine kit comprising:

(1) a first container, and the mesenchymal stem cell according to the first aspect of the present invention contained therein; and (2) a second container, and an antitumor immunotherapy agent contained therein.

In another preferred embodiment, the antitumor immunotherapy agent is selected from the group consisting of an antibody, an immune cell, and a combination thereof.

In another preferred embodiment, the immune cell is a T cell or NK cell.

In another preferred embodiment, the antitumor immunotherapy agent is an immune checkpoint antibody.

In another preferred embodiment, the immune checkpoint antibody includes a PD-1 antibody and/or a CTLA-4 antibody.

The present invention also provides a method for treating a disease, comprising administering an appropriate amount of cells according to the first aspect of the present invention, or a preparation according to the third aspect of the present invention, or a combination of drugs according to the fifth aspect of the present invention to the subject in need of treatment.

In another preferred embodiment, the disease is a cancer or a tumor, preferably a solid tumor, more preferably a colorectal cancer.

It should be understood that, within the scope of the present invention, the technical features specifically described above and below (such as the Examples) can be combined with each other, thereby constituting a new or preferred technical solution which needs not be described one by one.

DESCRIPTION OF THE FIGURES

FIG. 1A, Expression of surface molecules of adipose mesenchymal stem cells detected by flow cytometry. FIG. 1B, Migration of MSC-GFP in vivo in a mouse model of CT26 subcutaneous transplanted tumors. MSC-GFP infiltration in tumor tissue detected by immunofluorescence, wherein green indicates MSC-GFP, blue (DAPI stain) indicates nucleus. Scale bars, 20 μm. FIG. 1C, The specific number of MSC-GFP in the whole CT26 subcutaneous transplanted tumor detected by flow cytometry. The data represent mean±SEM (n=3).

FIG. 2A, Overexpression of CCL3 and CXCL9 in CT26 detected by WB and qPCR. The data represent mean±SEM (n=3). FIG. 2B, Cell proliferation experiments of CT26-Vector, CT26-CCL3 and CT26-CXCL9. The data represent mean±SEM (n=3). FIG. 2C, Tumor growth curves of BALB/c mice subcutaneously injected with CT26-Vector, CT26-CCL3, or CT26-CXCL9 tumor cells; tumor sizes were measured every 3 days. The data represent mean±SEM (n=4). FIG. 2D, Percentage of CD8+, CD4+ T, and NK cells in total cells. The data represent mean±SEM (n=4).

FIG. 3A, Overexpression of IL36β and OX40L in CT26 detected by WB. FIG. 3B, Overexpression of OX40L in CT26 detected by flow cytometry. FIG. 3C, Cell proliferation experiments of CT26-Vector, CT26-IL36β and CT26-OX40L. The data represent mean±SEM (n=3). FIG. 3D, Tumor growth curves of BALB/c mice subcutaneously injected with CT26-Vector, CT26-CCL3, or CT26-CXCL9 tumor cells; tumor sizes were measured every 3 days. Each group contains 4 mice. The data represent mean±SEM (n=4). * $p<0.05$, ** $p<0.01$.

FIG. 4A, Overexpression of CXCL9 in MSC detected by WB. FIG. 4B, Overexpression of CXCL9 in MSC detected by ELISA. The data represent mean±SEM (n=3). *** $p<0.001$.

FIG. 4C, Overexpression of OX40L in MSC detected by WB. FIG. 4D, Overexpression of OX40L in MSC detected by flow cytometry.

FIG. 5A, Secretion of CXCL9 detected by ELISA. FIG. 5B, Expression of OX40L detected by flow cytometry. FIG. 5C, The sizes of CT26 subcutaneous xenograft at different time points are shown in the figure. The arrows indicate the corresponding times of PBS or MSC injection to the mice. The data represent mean±SEM (n=5). FIG. 5D, Proportion of immune cells in tumors after MSC treatment analyzed by flow cytometry. * $p<0.05$,  $p<0.01$, * $p<0.001$, ns=not significant.

FIG. 6A, Scheme of AOM/DSS treatment and MSC treatment schedule. FIG. 6B, Representative images of colorectal tumors. Scale bar, 5 mm. FIG. 6C, Mean tumor numbers and sizes. The data represent mean±SEM (n=3 to 4). * $p<0.05$,  $p<0.01$, * $p<0.001$, ns=not significant. FIG. 6D, Immunofluorescence staining of CD8 and NK cells. Scale bar: 50 μm.

FIG. 7A, Scheme of AOM/DSS treatment and antibody treatment schedule. FIG. 7B, Mean tumor numbers and sizes. The data represent mean±SEM (n=4). ns=not significant.

FIG. 8A, Scheme of mesenchymal stem cells (MSC-CXCL9+OX40L) (5×105 cells per injection) and PD-1 antibody blocking (αPD-1) therapy; FIG. 8B, Combined treatment of mesenchymal stem cells overexpressing CXCL9 and OX40L and PD-1 antibody blocking had a more significant tumor suppressive effect than the treatment of both alone (n=7-8 mice/group). ** $p<0.01$.

FIG. 9A, Flow cytometry analysis was performed on in vivo mouse colorectal cancer cell MC38 subcutaneous xenograft, and it was confirmed that MC38 tumor cells (sgB2m) knocked out the B2m gene did not express MHC-I molecules (H2Kb/H2Db) compared with the control sgLacZ (n=4 cells/group); FIG. 9B, A xenograft model expressing OVA of MC38-sgB2m with MHC-I deletion or control MC38-sgLacZ tumor cells was established in vivo, and it was found that MC38-sgB2m grew faster than the control MC38-sgLacZ cells normally expressed by MHC-I, and the tumor vaccine (OVA257-264 peptide plus poly: IC adjuvant) was used for treatment, and it was found that MC38-sgLacZ cells were significantly inhibited by tumor vaccines, while MC38-sgB2m tumors with MHC-I deletion did not respond to vaccine therapy (n=5 mice/group); FIG. 9C, Mesenchymal stem cells overexpressing CXCL9 and OX40L significantly inhibited the growth of MC38-sgB2m tumors with MHC-I deletion (n=7 mice/group).  $p<0.01$, * $p<0.001$, **** $p<0.0001$.

FIG. 10A, Mesenchymal stem cells overexpressing GITRL, 4-1BBL or CD40L had a very significant tumor suppressive effect, while mesenchymal stem cells overexpressing IL5 had no significant therapeutic effect (n=5 cells/group); FIG. 10B, Mesenchymal stem cells overexpressing CCL3, CCL19, CCL21 or XCL1 had significant tumor suppressive effect (n=5 mice/group). * $p<0.05$, *** $p<0.01$, * $p<0.001$

DETAILED DESCRIPTION

Figure 1A:
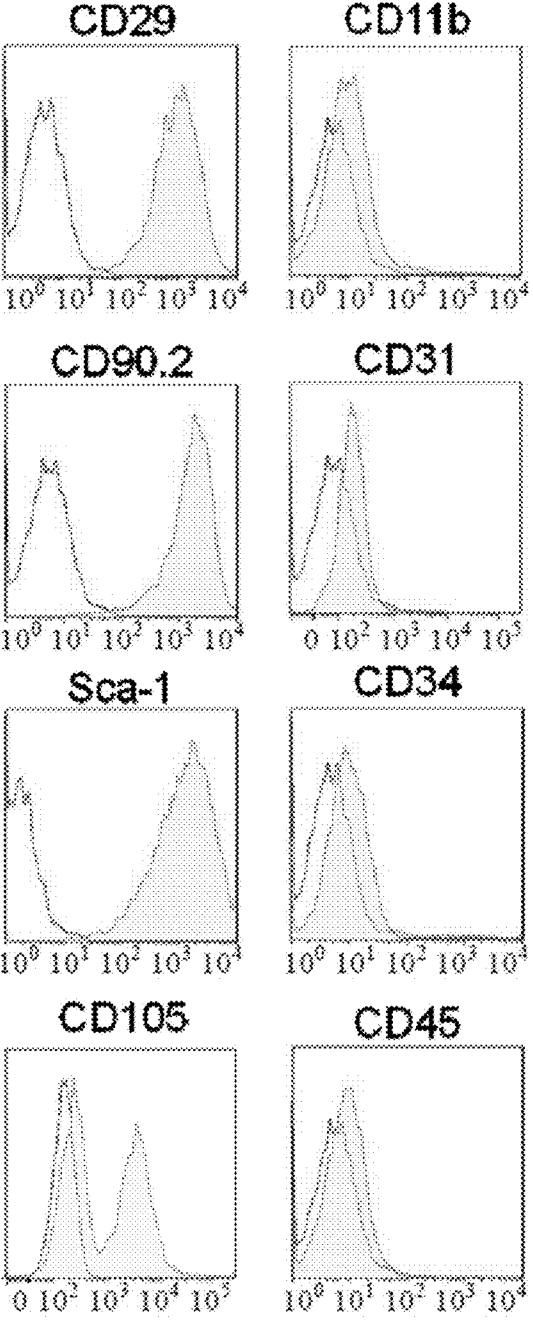
FIG. 1A to FIG. 1C show the identification of phenotype and migration to tumors of mouse adipose mesenchymal stem cells.

Through extensive and intensive research, the inventors unexpectedly discovered for the first time that, when the mesenchymal stem cells overexpress chemokines CCL3, CCL19, CCL21, XCL1, CXCL9 and/or cytokines OX40L, 4-1BBL, GITRL, CD40L, they can specifically attract and activate immune cells that kill tumor tissues at the tumor site, and the mesenchymal stem cells have a synergistic effect with chemokines and/or cytokines, with more efficient immune efficacy and low side effects. In particular, when mesenchymal stem cells overexpress CXCL9 and OX40L, they have synergistic effects and their killing ability of tumor tissues, especially colorectal cancer cells, is significantly enhanced. On this basis, the present invention has been completed by the inventors.

In recent years, immunotherapyies such as cytokines, CAR-T cells or immune checkpoint blockade have produced good efficacy in some cancer patients, but have also encountered many obstacles, such as the low reaching efficiency of T cells to the tumor site, small number of immune cells in the tumor site, side effects caused by systemic medication and the like. Mesenchymal stern cells can be obtained from a variety of tissues in vivo, and are easy to culture, expand, and modified via genetic engineering in vitro, with low immunogenicity. The inventor's research in mouse models confirmed that adipose mesenchymal stem cells can migrate specifically to the tumor site and are not enriched in other organs, thus they can be used as an ideal drug carrier. Adipose mesenchymal stem cells are used in the present invention as a carrier to overexpress the chemokine CXCL9 and cytokine OX40L having immunomodulatory effect. Through the active migration to the tumor and the specifically attraction and activation of immune cells that kill tumor tissues at the tumor site of the mesenchymal stem cells, more efficient immunotherapy efficacy and lower side effects are finally achieved.

Terms

Unless otherwise defined, all technical and scientific terms used herein have the same meaning as would normally be understood by those of ordinary skill in the art to which the invention belongs.

As used herein, term "about" means that the value may change by no more than 1% from the enumerated value when used in reference to a specific enumerated value. For example, as used herein, the expression "about 100" includes all values between 99 and 101 and (e.g., 99.1, 99.2, 99.3, 99.4, etc.).

As used herein, term "contain" or "include (comprise)" may be open, semi-closed, and closed. In other words, said term also includes "consisting essentially of" or "consisting of".

As used herein, the term "administration" refers to the physical introduction of the product of the present invention into the subject using any one of the various methods and delivery systems known to those skilled in the art, including intravenous, intramuscular, subcutaneous, intraperitoneal, spinal cord or other parenteral administration routes, such as by injection or infusion.

Mesenchymal Stem Cell (MSC)

In recent years, mesenchymal stem cells (MSCs) have emerged as potential cell carriers, with the ability to actively migrate to many different tumor types when administered systemically. It can be extracted from many different adult tissues, easy to expand and culture, and can avoid immune rejection. Meanwhile, the characteristics of tumor-targeting migration and long-term survival at the target site of the mesenchymal stem cell make it an important resource for cell therapy. The commonly used types of MSCs are bone marrow-derived MSCs (BM-MSCs), umbilical cord blood-derived MSCs (UCB-MSCs), umbilical cord-derived MSCs (UC-MSCs), and adipose tissue-derived MSCs (AT-MSCs). However, the isolation process of BM-MSCs and UCB-MSCs are complex and inefficient. Therefore, adipose tissue or umbilical cord tissue MSCs can be used as more ideal alternatives, because they contain more MSCs than bone marrow and umbilical cord blood, and the tissues are easier to obtain and collect. In addition, with regard to the source of autologous stem cells used for individualized cell therapy, AT-MSCs have minimal risk to donors and no ethical issues.

Through the tumor homing ability of MSCs, MSCs are used in the present invention to targeted delivery of chemokine CCL3, CCL21, XCL1, CXCL9 and cytokines OX40L, 4-1BBL, GITRL, CD40L to attract and activate effector T cells, NK cells and antigen-presenting cells in the tumor microenvironment, so as to produce more precise and sustained immune response to kill tumor cells. In the current study, adipose mesenchymal stem cells are used as the carrier to overexpress chemokine and cytokine to treat colorectal cancer in mouse models.

Expression Cassette

As used herein, "expression cassette" or "expression cassette of the present invention" includes a first expression cassette and/or a second expression cassette. The first expression cassette comprises a nucleic acid sequence of a chemokine, and the second expression cassette comprises a nucleic acid sequence encoding a cytokine, wherein the chemokine includes: CCL3, CCL19, CCL21, XCL1, CXCL9, and a combination thereof, and the cytokine includes: OX40L, 4-1BBL, GITRL, CD40L, and a combination thereof.

In one embodiment, the exogenous nucleic acid molecule comprises a first expression cassette and a second expression cassette, wherein the first expression cassette comprises a nucleic acid sequence encoding CXCL9, and the second expression cassette comprises a nucleic acid sequence encoding OX40L.

In another preferred embodiment, the first expression cassette and the second expression cassette are independent or connected. In another preferred embodiment, the first expression cassette and the second expression cassette further include a promoter and/or a terminator, respectively. In another preferred embodiment, the first expression cassette and the second expression cassette are on a vector or integrated into a chromosome of the mesenchymal stem cell. In another preferred embodiment, the first expression cassette and the second expression cassette are in the same or different vectors. In another preferred embodiment, the first expression cassette and the second expression cassette are in the same vector. In another preferred embodiment, the vector is selected from the group consisting of DNA, RNA, plasmid, lentiviral vector, adenoviral vector, retroviral vector, transposon, other gene transfer system, and a combination thereof.

Vector

The present invention further provides a vector containing the expression cassette of the present invention. Vectors derived from retroviruses such as lentiviruses are suitable tools to achieve long-term gene delivery, because they allow long-term and stable integration of transgenes and propagation in daughter cells. The lentiviral vectors have advantages over vectors derived from oncogenic retroviruses such as murine leukemia viruses, because they can transduce non-proliferating cells such as hepatocytes. They also have the advantage of low immunogenicity.

Briefly summarized, the expression cassette or nucleotide sequence of the present invention is usually operably linked to a promoter and incorporated into an expression vector. The vector is suitable for replication and integration of eukaryotic cell. A typical cloning vector contains a transcription and translation terminator that can be used to regulate the expression of a desired nucleotide sequence, an initial sequence, and a promoter.

The expression construct of the present invention can also be used for nucleic acid immunization and gene therapy by using standard gene delivery schemes. Methods of gene delivery are known in the art. See, for example, U.S. Pat. Nos. 5,399,346, 5,580,859, 5,589,466, which are hereby incorporated by reference in their entirety. In another embodiment, the present invention provides a gene therapy vector.

The expression cassette or nucleic acid can be cloned into many types of vectors. For example, the expression cassette or nucleic acid can be cloned into such vectors, which include, but are not limited to, plasmids, phagemids, phage derivatives, animal viruses, and cosmids. Specific vectors of interest include expression vectors, replication vectors, probe generation vectors, and sequencing vectors.

Further, the expression vectors can be provided to cells in the form of viral vectors. The viral vector technology is well known in the art and is described in, for example, Sambrook et al. (2001, Molecular Cloning: A Laboratory Manual, Cold Spring Harbor Laboratory, New York) and other virology and molecular biology manuals. Viruses that can be used as vectors include, but are not limited to, retroviruses, adenoviruses, adeno-associated viruses, herpes viruses, and lentiviruses. Generally, a suitable vector contains an origin of replication that functions in at least one organism, a promoter sequence, a convenient restriction enzyme site, and one or more optional markers (e.g., WO01/96584; WO01/29058; and U.S. Pat. No. 6,326,193).

Many virus-based systems have been developed for delivering gene into mammalian cells. For example, retroviruses provide a convenient platform for gene delivery systems. The selected gene can be inserted into a vector and packaged into a retrovirus particle by using a technology known in the art. The recombinant virus can then be isolated and transferred to an object cell in vivo or ex vivo. Many retrovirus systems are known in the art.

Additional promoter components, such as enhancers, can regulate the frequency of transcription initiation. Generally, these are located in a 30-110 bp region upstream of the initiation site, although it has recently been shown that many promoters also contain functional components downstream of the initiation site. The spacing between the promoter components is often flexible in order to maintain promoter functions when one component is inverted or moved relative to the other one. In a thymidine kinase (tk) promoter, the activity does not begin to decrease until that the spacing between promoter components can be increased by 50 bp.

Depending on the promoter, it appears that individual components can act cooperatively or independently to initiate transcription.

An example of a suitable promoter is an early cytomegalovirus (CMV) promoter sequence. The promoter sequence is a strong constitutive promoter sequence capable of driving high-level expression of any polynucleotide sequence operably linked thereto. Another example of a suitable promoter is an elongation growth factor-1α (EF-1α). However, other constitutive promoter sequences can also be used, including but not limited to simian virus 40 (SV40) early promoters, mouse mannary tumor virus (MMTV) and human immunodeficiency virus (HIV) long terminal repeat (LTR) promoters, MoMuLV promoters, avian leukemia virus promoters, Epstein-Barr virus immediate early promoters, Ruth's sarcoma virus promoters, and human gene promoters, such as but not limited to actin promoters, myosin promoters, heme promoters and creatine kinase promoters. Further, the present invention should not be limited to the application of constitutive promoters. Inducible promoters are also considered part of the present invention. The use of an inducible promoter provides a molecular switch that can turn on expression of a polynucleotide sequence operably linked to the inducible promoter when such expression is desired, or turn off the expression when the expression is not desired. Examples of the inducible promoters include, but are not limited to, metallothionein promoters, glucocorticoid promoters, progesterone promoters and tetracycline promoters.

The expression vector introduced into the cell may also contain either or both of an optional marker gene or a reporter gene, so as to identify and select an expression cell from a transfected or infected cell population sought through a viral vector. In other aspects, the optional marker can be carried on a single segment of DNA and used in a co-transfection procedure. Both the optional marker and reporter gene can be flanked by appropriate regulatory sequences to enable expression in the host cell. Useful optional markers include, for example, antibiotic resistance genes such as neo.

Reporter genes are used to identify potentially transfected cells and to evaluate the functionality of regulatory sequences. Generally, a reporter gene is a gene that does not exist in or is expressed by a receptor organism or tissue, and encodes a polypeptide whose expression is clearly indicated by some easily detectable properties such as enzyme activity. After the DNA is introduced into the receptor cell, the expression of the reporter gene is measured at an appropriate time. Suitable reporter genes may include genes encoding luciferase, β-galactosidase, chloramphenicol acetyltransferase, secreted alkaline phosphatase, or green fluorescent protein (e.g., Ui-Tei et al., 2000 FEBS Letters 479: 79-82). Suitable expression systems are well known and can be prepared by using known techniques or obtained commercially. Generally, a construct with a minimum of 5 flanking regions that shows the highest level of reporter gene expression is identified as a promoter. Such a promoter region can be linked to a reporter gene and used to evaluate the ability of a reagent to regulate the promoter-driven transcription.

Methods of introducing and expressing genes into cells are known in the art. In the content of the expression vector, the vector can be easily introduced into a host cell, for example, a mammalian (e.g., a human T cell), bacteria, yeast, or insect cell, by any method in the art. For example, the expression vector can be transferred into the host cell by physical, chemical or biological means.

Physical methods of introducing polynucleotides into host cells include calcium phosphate precipitation, lipofection, particle bombardment, microinjection, electroporation, etc. Methods of producing cells comprising vectors and/or exogenous nucleic acids are well known in the art. See, for example, Sambrook et al. (2001, Molecular Cloning: A Laboratory Manual, Cold Spring Harbor Laboratory, New York).

Biological methods for introducing polynucleotides into host cells include the use of DNA and RNA vectors. Viral vectors, especially retroviral vectors, have become the most widely used method of inserting genes into mammalian cells such as human cells. Other viral vectors can be derived from lentivirus, poxvirus, herpes simplex virus I, adenovirus, adeno-associated virus, etc. See, for example, U.S. Pat. Nos. 5,350,674 and 5,585,362.

Chemical methods for introducing polynucleotides into host cells include colloidal dispersion systems, such as macromolecular complexes, nanocapsules, microspheres, and beads; and lipid-based systems, including oil-in-water emulsions, micelles, mixed micelles, and liposomes. Exemplary colloidal systems used as delivery vehicles in vitro and in vivo are liposomes (e.g., artificial membrane vesicles).

When a non-viral delivery system is used, an exemplary delivery vehicle is liposome. Lipid preparation is considerable to introduce nucleic acids into host cells (in vitro, ex vivo or in vivo). In another aspect, the nucleic acids can be associated with lipids. A lipid-associated nucleic acid can be encapsulated in the aqueous interior of a liposome, dispersed in the lipid bilayer of the liposome, attached to the liposome via a linker molecule associated with both the liposome and an oligonucleotide, trapped in the liposome, complexed with the liposome, dispersed in a lipid-containing solution, mixed with the lipid, combined with the lipid, contained in the lipid as a suspension, contained in micelles or complexed with micelles, or associated with the lipid in other way. The lipid, lipid/DNA or lipid/expression vector associated with a composition is not limited to any specific structure in the solution. For example, they may exist in a bimolecular structure as micelles or have a "collapsed" structure. They can also be simply dispersed in the solution, which may form aggregates of uneven size or shape. Lipids are fatty substances, which can be naturally occurring or synthetic lipids. For example, the lipids include fat droplets, which occur naturally in cytoplasms and in such compounds containing long-chain aliphatic hydrocarbons and their derivatives such as fatty acids, alcohols, amines, amino alcohols and aldehydes.

Preparation Method

The present invention provides a method for preparing a mesenchymal stem cell, comprising introducing a first expression cassette and/or a second expression cassette into the mesenchymal stem cell to be modified, wherein the first expression cassette is used to express chemokines, and the second expression cassette is used to express cytokines, thereby obtaining the mesenchymal stem cell.

Generally, it comprises the following steps: (1) transforming or transducing suitable host cells with the polynucleotides encoding immunostimulatory factors of the present invention, or with recombinant expression vectors containing the polynucleotides; (2) culturing the host cells in suitable medium.

Preparation

The present invention provides a preparation comprising the mesenchymal stem cell according to the first aspect of the present invention, and a pharmaceutically acceptable carrier, diluent or excipient. In one embodiment, the preparation is a liquid preparation. Preferably, the preparation is an injection. Preferably, the concentration of the mesenchymal stem cell in the preparation is $1\times10^3$-$1\times10^8$ cells/ml, preferably $1\times10^4$-$1\times10^7$ cells/ml.

In one embodiment, the preparation may comprise a buffer such as neutral buffered saline, or sulfate buffered saline etc.; a carbohydrate such as glucose, mannose, sucrose or dextran, or mannitol; a protein; a polypeptide or amino acid such as glycine; an antioxidant; a chelating agent such as EDTA or glutathione; an adjuvant (for example, aluminum hydroxide); and a preservative. The preparation of the present invention is preferably prepared for intravenous administration.

Therapeutic Application

The present invention comprises a therapeutic application of the mesenchymal stem cell transduced with a vector containing the expression cassette of the present invention. Mesenchymal stem cells of the present invention can actively migrate to the tumor site, and are not enriched in organs such as liver, spleen and kidney, and have specificity and safety as a carrier for tumor treatment drugs, providing an effective means for local activation of immune responses in tumors to avoid systemic side effects. The adipose mesenchymal stem cell therapy system overexpressing the chemokine CXCL9 and cytokine OX40L has the characteristics of specifically targeting the tumor site, attracting and activating T cells and NK cells to achieve ideal anti-tumor efficacy.

In one embodiment, the present invention provides a type of cell therapy comprising administering the mesenchymal stem cell of the present invention to a mammal. Unlike antibody therapy, the mesenchymal stem cell of the present invention can replicate in vivo to achieve long-term persistence that can lead to sustained tumor control.

Cancers that can be treated include tumors that have not been vascularized or have not been substantially vascularized, as well as vascularized tumors. The cancers may include non-solid tumors (for example, hematological tumors such as leukemia and lymphomas) or solid tumors. The cancer types treated with the mesenchymal stem cell of the present invention include, but are not limited to, carcinomas, blastomas and sarcomas, and some leukemia or lymphoid malignancies, benign and malignant tumors, and malignant tumors, such as sarcomas, cancers, and melanomas. Adult tumors/cancers and childhood tumors/cancers are also included.

The hematological cancers are cancers of the blood or bone marrow. Examples of the hematological (or hematogenic) cancers include leukemia, including acute leukemia (such as acute lymphoblastic leukemia, acute myelocytic leukemia, acute myeloid leukemia and meroblastic, promyelocytic, myelomonocytic, monocytic and erythroleukemia), chronic leukemia (such as chronic myelocytic (granulocyte) leukemia, chronic myeloid leukemia, and chronic lymphocytic leukemia), polycythemia vera, lymphoma, Hodgkin's disease, non-Hodgkin's lymphoma (painless and high-grade forms), multiple myeloma, Waldenstrom's macroglobulinemia, heavy chain diseases, myelodysplastic syndromes, hairy cell leukemia, and myelodysplasia.

The solid tumors are abnormal lumps that usually do not contain cysts or tissues of fluid regions. The solid tumors may be benign or malignant. Different types of solid tumors are named by cell types that form them (such as sarcomas, carcinoma, and lymphomas). Examples of the solid tumors such as sarcomas and carcinoma include: fibrosarcoma, myxosarcoma, liposarcoma, mesothelioma, lymphoid malignancy, pancreatic carcinoma and ovarian carcinoma.

The mesenchymal stem cells of the present invention can also be used as a type of vaccines for ex vivo immunization and/or in vivo therapy of mammals. Preferably, the mammals are humans.

For ex vivo immunization, at least one of the following occurs in vitro before the cells are administered into the mammals: i) expanding the cells, ii) introducing the expression cassette of the present invention into the cells, and/or iii) cryopreserving the cells.

Ex vivo procedures are well known in the art and will be discussed more fully below. Briefly, cells are isolated from mammals (preferably humans) and genetically modified (i.e., transduced or transfected in vitro) with vectors containing the expression cassette of the preset invention. The mesenchymal stem cells of the present invention can be administered to a mammalian recipient to provide therapeutic benefits. The mammalian recipient may be a human, and the mesenchymal stem cells may be autologous relative to the recipient. Alternatively, the cells may be allogeneic, syngeneic, or xenogeneic relative to the recipient.

In addition to the use of cell-based vaccines for ex vivo immunization, the present invention also provides a composition and method for in vivo immunization to cause an immune response against an antigen in a patient.

In general, activated and expanded cells as described herein can be used to treat and prevent diseases developing in individuals without immune response. The present invention therefore provides a method for treating tumors, which includes administering an effective dose of mesenchymal stem cells of the present invention to a subject in need.

The mesenchymal stem cells of the present invention can be administered alone or as a pharmaceutical composition administered with diluent and/or with other components or other cytokines or cell populations. Briefly, the pharmaceutical composition of the present invention may include mesenchymal stem cells as described herein, and one or more pharmaceutically or physiologically acceptable carriers, diluents or excipients.

The pharmaceutical composition of the present invention can be administered in a manner suitable for a disease to be treated (or prevented). The number and frequency of administration are determined by the factors such as patient's condition, and the type and severity of the patient's disease, although the appropriate dose can be determined by clinical trials.

When referring to "immunologically effective dose", "anti-tumor effective dose", "tumor-suppressive effective dose" or "therapeutic dose", the precise dose of the composition of the present invention to be administered can be determined by the physician, who considers individual differences of patients (subjects) in age, weight, tumor size, degree of infection or metastasis, and symptom. It may generally be pointed out that the pharmaceutical composition containing the mesenchymal stem cells described herein may be administered at a dose of $10^4$ to $10^9$ cells/kg body weight, preferably a dose of $10^5$ to $10^6$ cells/kg body weight (including all integer values in those ranges). The mesenchymal stem cell composition may also be administered multiple times at these doses. The cells can be administered by using injection techniques well known in immunotherapy (see, for example, Rosenberg et al., New Eng. J. of Med. 319:1676, 1988). The optimal dose and therapeutic schedule for a specific patient can be easily determined by a person skilled in the medical field by monitoring patient's signs of disease and adjusting the treatment accordingly.

The object composition can be administered in any convenient manner, including by spraying, injection, swallowing, infusion, implantation or transplantation. The composition described herein can be administered subcutaneously, intracutaneously, intratumorally, intranodally, intraspinally, intramuscularly, by intravenous (i.v.) injection or intraperitoneally to the patient. In one embodiment, the T cell composition of the present invention is administered to the patient by intradermal or subcutaneous injection. In another embodiment, the T cell composition of the present invention is preferably administered by i.v. injection. The composition of mesenchymal stem cell can be injected directly into tumors, lymph nodes or sites of infection.

In some embodiments of the present invention, cells activated and expanded using the methods described herein or other methods known in the art for expanding mesenchymal stem cells to therapeutic levels are administered to the patient in combination with any number of relevant treatment forms (e.g., before, at the same time or after). The treatment forms include but are not limited to treatment with the following reagents: the reagents such as antiviral therapy, cidofovir and interleukin-2, cytarabine (also known as ARA-C) or natalizumab treatment for MS patients or efalizumab treatment for psoriasis patients or other treatments for PML patients. In a further embodiment, the mesenchymal stem cells of the present invention can be used in combination with chemotherapy, radiation, immunosuppressive agents, such as cyclosporine, azathioprine, methotrexate, mycophenolate mofetil and FK506, antibodies or other immunotherapeutic agents. In a further embodiment, the cell composition of the present invention is administered to the patient in combination with bone marrow transplantation, chemotherapeutic agents such as fludarabine, external beam radiotherapy (XRT), or cyclophosphamide (e.g., before, at the same time or after). For example, in one embodiment, the subject can undergo standard treatment of high-dose chemotherapy, followed by peripheral blood stem cell transplantation. In some embodiments, after transplantation, the subject receives an infusion of the expanded mesenchymal stem cells of the present invention. In an additional embodiment, the expanded cells are administered before or after surgery.

The dose of the above treatment administered to the patient varies with the precise nature of the condition being treated and the recipient of the treatment. The dose ratio for human administration can be implemented according to the practice accepted in the art. Generally, $1\times10^3$ to $1\times10^9$ mesenchymal stem cells of the present invention can be administered to the patient per treatment or per course of treatment, for example, by intravenous infusion.

The Technical Solution of the Present Invention has the Following Advantages

1. The mesenchymal stem cells of the present invention can be obtained from a variety of tissues in vivo, and are easy to culture, expand, and be modified via genetic engineering in vitro, with low immunogenicity.

2. Compared with most immunotherapies, the method of the present invention does not depend on the existence of tumor infiltrating lymphocytes, and is also applicable to the treatment of tumors with very low or resistance of lymphocyte infiltration in clinical practice.

3. When the mesenchymal stem cells of the present invention overexpress one or more of CCL3, CCL19, CCL21, XCL1, CXCL9, OX40L, 4-1BBL, GITRL and CD40L, they can specifically attract and activate immune cells that kill tumor tissue at the tumor site, and have a more efficient immune efficacy and low side effects.

4. When the mesenchymal stem cells of the present invention overexpress CXCL9 and OX40L, they have a synergistic effect and their killing ability of tumor tissues, especially colorectal cancer cells, is significantly enhanced. This method can also kill MHC-1 negative tumor cells with resistance to traditional immunotherapy (such as CAR-T or PD-1/PD-L1 antibody).

5. When the present invention is combined with other immunotherapies used in clinic, such as CAR-T or PD-1/PD-L1 antibody, it can also enhance the efficacy of these it munotherapies. The combined treatment of mesenchymal stem cells of the present invention and PD-1 antibody has more significant tumor inhibition effect than the single treatment of the two, and the two show a synergistic effect.

The following further illustrates the present invention in combination with specific examples. It should be understood that these examples are only used for explaining the present invention, rather than limiting the scope of the present invention. The experimental methods unmarked with specific conditions in the following examples were carried out according to conventional conditions, for example, the conditions described in Sambrook et al., Molecular Cloning: A Laboratory Manual (New York: Cold Spring Harbor Laboratory Press, 1989), or according to the conditions recommended by the manufacturers. Unless otherwise specified, the percentages and parts were calculated by weight.

Materials and Methods

Cell Lines

CT26 cells are colon adenocarcinoma cells derived from BALB/c mice, and MC38 cells are colon adenocarcinoma cells derived from C57BL/6 mice. CT26 and MC38 cells were respectively cultured in RPMI 1640 and DMEM supplemented with 10% fetal bovine serum (FBS) and 1% penicillin/streptomycin.

Antibody

The antibodies used for flow cytometry were from BD Biosciences, BioLegend, or eBioscience. Antibodies used for western blotting include anti-CXCL9 (Abeam), anti-Myc-tag (Cell Signaling Technology), anti-OX40L (Abeam) and anti-GAPDH (Abeam). Antibodies used for immunofluorescence include anti-CPP (Abeam), anti-CD8a (BioLegend), and anti-NKp46 (CD335) (BioLegend).

The immune checkpoint blocking antibodies anti-PD-1 (clone RMP1-4) and anti-CTLA-4 (clone 9D9) were purchased from Bio X Cell. Both of the two antibodies anti-PD-1: 200 μg/mouse; anti-CTLA-4: 100 μg/mouse) were administered to mice via intraperitoneal injection.

Isolation, Culture, and Identification of Mesenchymal Stem Cells from Mouse Adipose Tissue AT-MSCs were isolated from the mouse subcutaneous adipose tissue using collagenase type I. Cells were cultured in α-MEM medium supplemented with 10% FBS and 1% penicillin/streptomycin. The cells were adherent to culture for three passages, and the expression of cell surface marker proteins were identified via flow cytometry.

Lentivirus Production and Transduction cDNAs were cloned into lentiviral vectors. Lentiviruses were packaged and titrated by OBiO Technology (Shanghai) Corp., Ltd. Mesenchymal stem cells were infected with lentiviruses at a multiplicity of infection (MOI) of 60 in the presence of 6 μg/mL polyrene (Sigma-Aldrich).

Cell Proliferation Experiment

Tumor cell proliferation was assessed by using CCK-8 kit (Dojindo Molecular Technologies) according to the specification. Absorbance was measured by using a microplate reader (Tecan).

Western Blotting

Cells were harvested and treated using cell lysis buffer (RIPA buffer+1% protease inhibitor) (Thermo Fisher Scientific) to prepare the cell lysates. Protein concentration of the cell lysates was determined by using a BCA kit (Thermo Fisher Scientific). 15-30 μg of proteins were loaded to 5%-15% SDS-PAGE protein gel (Thermo Fisher Scientific) and then transferred to PVDF membrane (Millipore). The membrane was blocked with 5% skim milk prepared in TBST buffer, and incubated overnight at 4° C. together with antibodies for Myc tag, OX40L, CXCL9, and GAPDH. The membrane was washed with TBS-T buffer and incubated with horseradish peroxidase-conjugated secondary antibody for 1 h at room temperature. The membrane was developed with an enhanced chemiluminescence kit (Millipore) and exposed to the membrane.

Enzyme-Linked Immunosorbent Assay (ELISA)

Supernatant of lentivirus-transduced AT-MSCs was collected and kept in a refrigerator at −80° C. until measurement. CXCL9 secretion was detected by using the ELISA kit (Abcam) according to the specification.

Mouse Subcutaneous Xenograft Model

CT26 or MC38 (0.5 or $1\times10^6$/mouse) cells were injected subcutaneously at the right lower back of 8 to 10-week-old BALB/c or C57BL/6 mice, respectively. Mice were grouped into experiment groups when tumor size reached 0.5-0.7 cm in the largest diameter. 250 μL of PBS or suspension of $5\times10^5$ AT-MSC in 250 μL of PBS was injected into the tail veins of each animal for systemic administration. Tumor sizes were measured every 3 days using a vernier caliper, and the tumor volumes were calculated using the following formula: $V=L\times W^2/2$, wherein L and W are the long and short diameters of tumor, respectively. Tumor size and survival rate of the mice were monitored. Mice were sacrificed when tumor reached 2 $cm^3$ in volume or became ulcerated, or when mice became moribund.

Flow Cytometry

To identify AT-MSC, adherent cells of passages 3 to 5 were isolated using 20 μM EDTA digestion, then washed twice with PBS and stained with antibodies.

To analyze tumor-infiltrating immune cells, subcutaneously implanted tumors were dissected and transferred into RPMI medium, broken with scissors, plated in serum-free RPMI medium containing 0.25 mg/ml Liberase TL (Roche) and 50 μg/ml DNase I (Sigma-Aldrich), digested using gentleMACS Octo Dissociator (Miltenyi Biotec) at 37° C., and dispersed through a 40-μm cell strainer (BD Biosciences). Single cells were further washed and stained with antibodies. Dead cells were excluded by staining with a Zombie Fixable Viability kit (BioLegend). For intracellular staining of cytokines, each mouse was intraperitoneally injected with 0.25 mg of brefeldectin A (BFA) (Selleck) 4-6 h prior to sample harvesting. After surface staining was performed in the presence of 5 μg/m1 of BFA, intracellular staining was performed with an intracellular fixation and permeabilization buffer set (eBioscience). Nuclear staining was performed with Foxp3 transcription factor staining buffer (eBioscience) after surface staining.

Fluorescence data were obtained on a BD LSRFortessa cell analyzer (BD Biosciences) and analyzed using FlowJo software. All antibodies used for flow cytometry were purchased from BD Biosciences, BioLegend or eBioscience.

AOM/DSS-Induced Colorectal Tumor Model

BALB/c mice were intraperitoneally injected with AOM (12.5 mg/kg of body weight; Sigma-Aldrich) (14). After 1 week, mice were fed with drinking water supplemented with 3% DSS (MP Biomedicals) for 7 days, followed by 2 weeks of normal water. The DSS induction was continued for two additional cycles, and mice were sacrificed after five injections of MSCs in the tail vein, starting from the last week of the DSS induction cycle. Body weights were recorded during DSS treatment. Colons were collected from mice, flushed with cold PBS, opened longitudinally, fixed overnight at room temperature in 4% paraformaldehyde solution (Sigma-Aldrich), and embedded with paraffin. Tumor sizes were measured using a digital caliper before fixation.

Immunofluorescence

Tissue sections were blocked with 10% normal goat serum and then incubated overnight with primary antibodies at 4° C. and incubated with secondary antibodies for 1 h at room temperature. Slides were mounted in anti-fade mounting reagent with DAPI (Thermo Fisher Scientific) and visualized under a Nikon Eclipse Ti fluorescence microscope. Antibodies used for immunofluorescence are GFP antibodies (Abcam), CD8a antibodies (BioLegend), and NKp46 antibodies (CD335) (BioLegend).

Statistic

All results are represented as mean±SEM. Differences were assessed by the Student t test, or when means of more than two groups were compared, by two-way ANOVA followed by a Bonferroni multiple comparison test. Data analyses were performed with Prism software (GraphPad). Statistical significance was set at the level of $p<0.05$.

Study Approval

All animal procedures were approved by the Animal Care and Use Committee of Shanghai Jiao Tong University.

Example 1 Property of Adipose Mesenchymal Stem Cells Migrating to Tumors

Figure 1B:
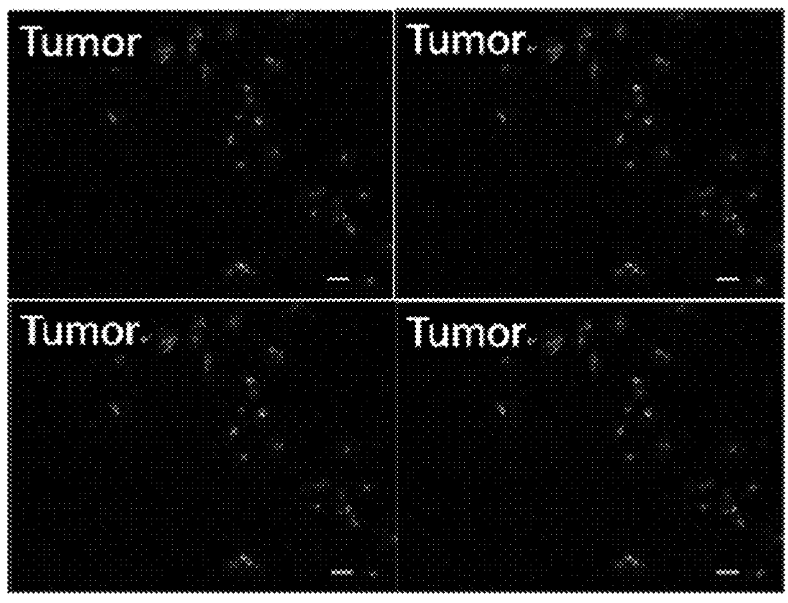
Figure 1C:
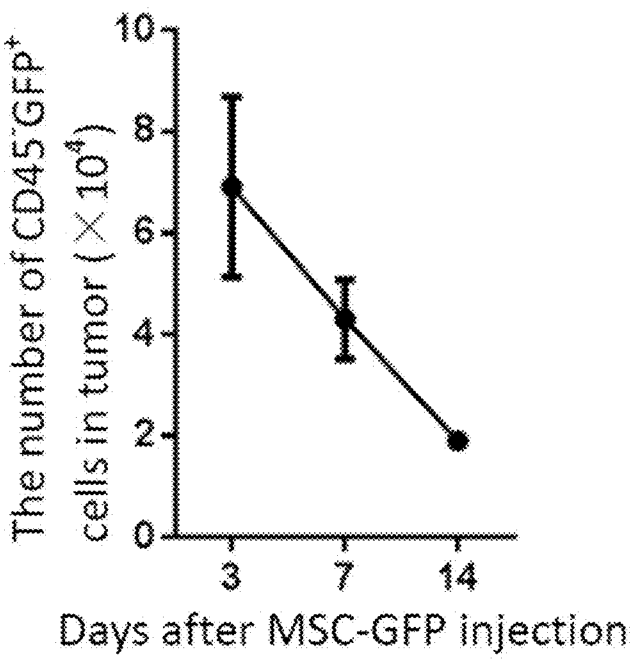

Mesenchymal stem cells were extracted from subcutaneous fat of mice. Through flow cytometry detection, these cells expressed specific mesenchymal stem cell marker molecules and did not express marker molecules of other cell types (FIG. 1A), which confirmed the purity of adipose mesenchymal stem cells used in the experiment. The adipose mesenchymal stem cells were transfected with lentivirus to express GFP, and then $5\times10^5$ cells were injected into the tumor-bearing mice (CT26 cancer subcutaneous tumor) through the tail vein. After 7 days, immunofluorescence staining was performed on the tumor and other organs. The results show that GFP-positive mesenchymal stem cells only reside in the tumor and are not found in other organs such as liver, spleen and kidney (FIG. 1B). The GFP-positive mesenchymal stem cells in tumor were detected via flow cytometry, and a certain number of cells could still be detected 14 days after cell injection (FIG. 1C). These results prove the properties that adipose mesenchymal stem cells specifically migrate to the tumor site and stay for a long time, supporting its potential as a carrier of therapeutic molecules.

Example 2 CXCL9 and OX40L Anti-Tumor Properties

Figure 2A:
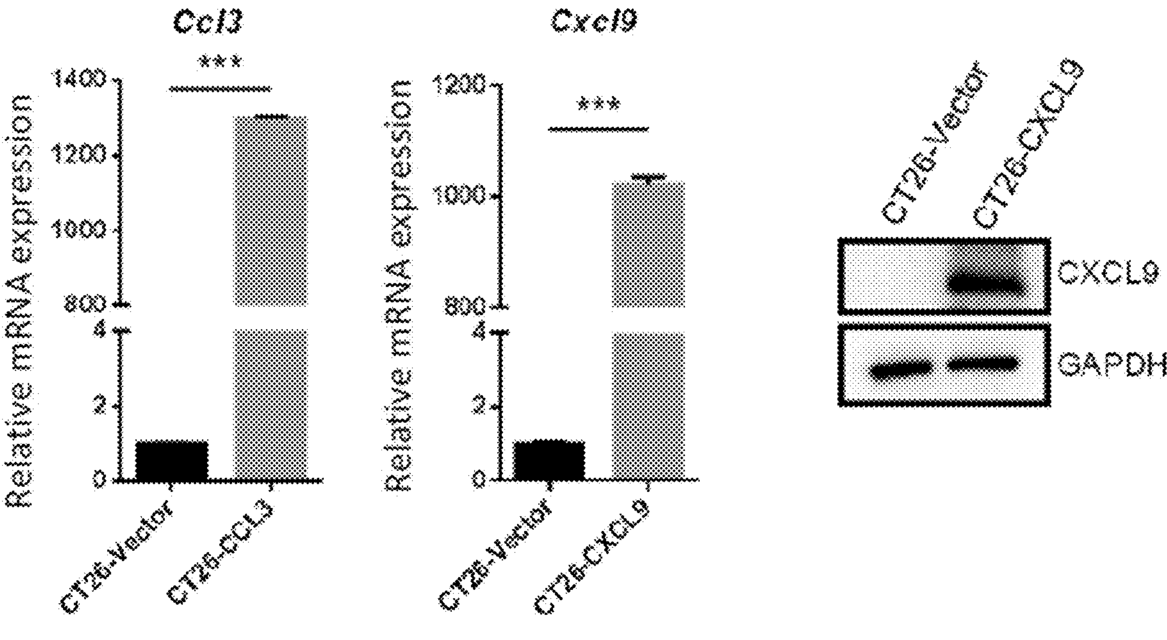
FIG. 2A to FIG. 2D show that overexpression of CXCL9 in tumor cells inhibits tumor growth in vivo.
Figure 2B:
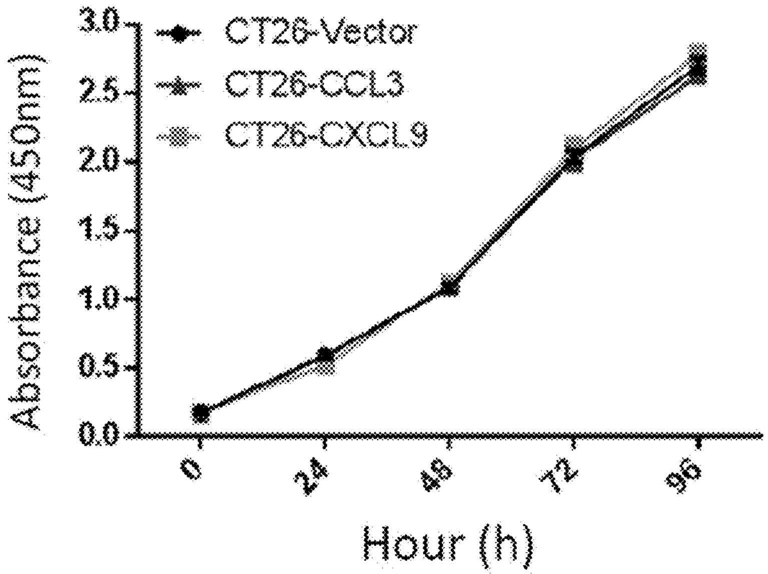
Figure 2C:
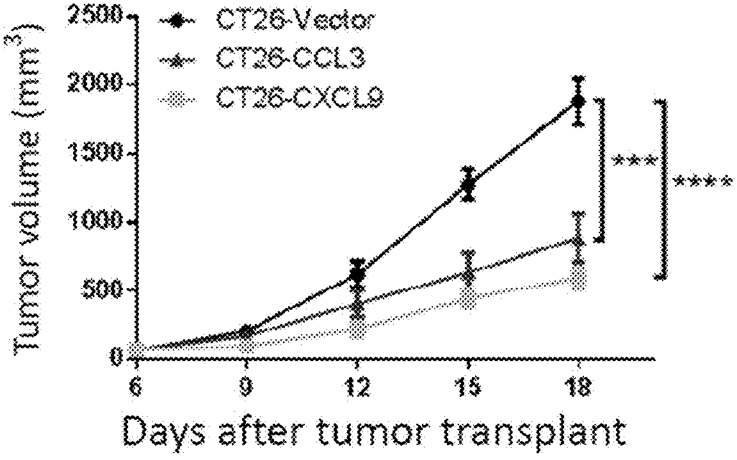
Figure 2D:
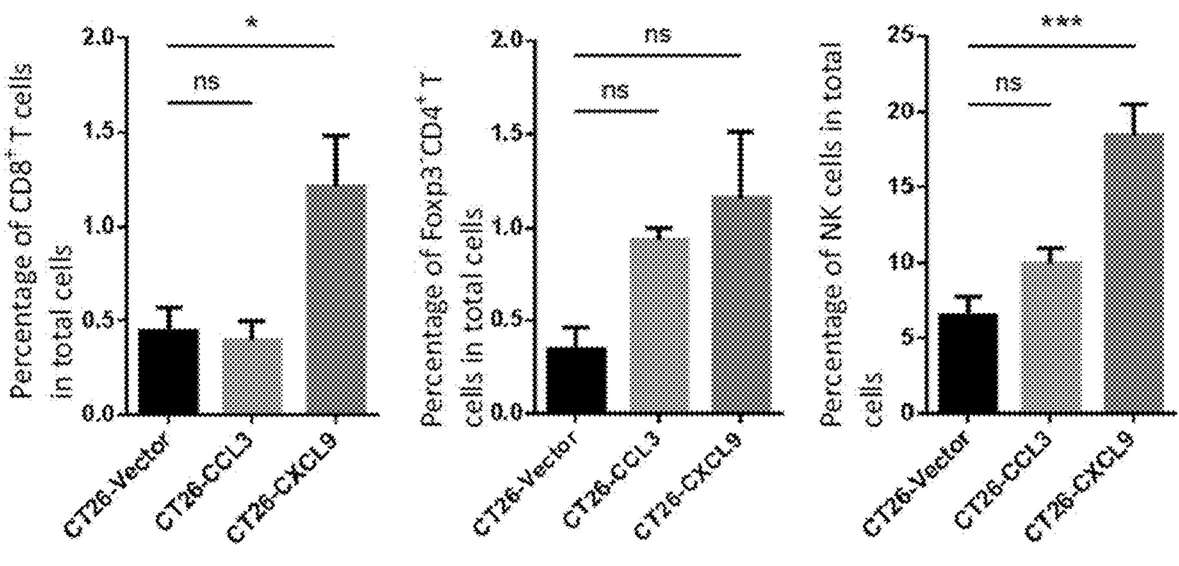
Figure 3A:
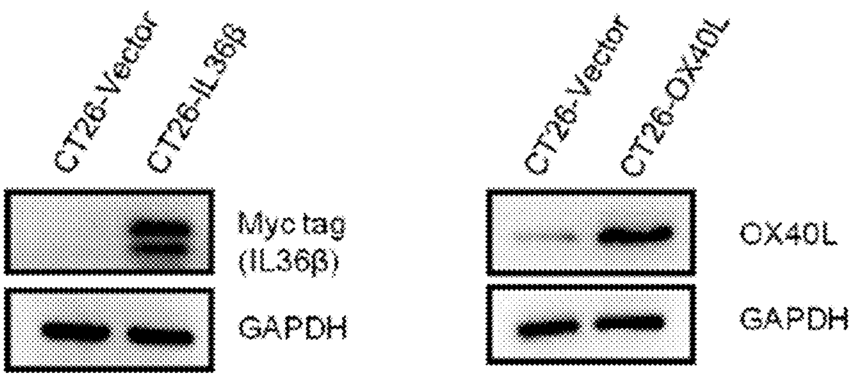
FIG. 3A to FIG. 3D show that overexpression of OX40L in tumor cells inhibits tumor growth in vivo.
Figure 3B:
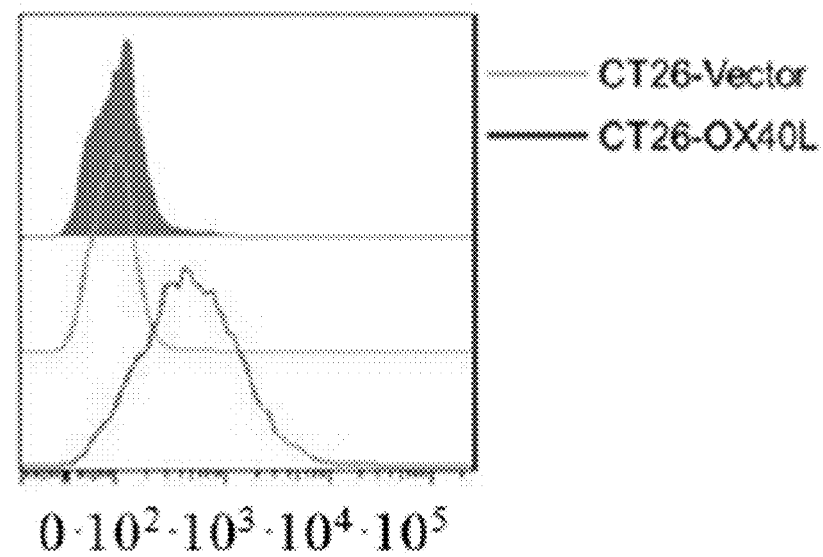
Figure 3C:
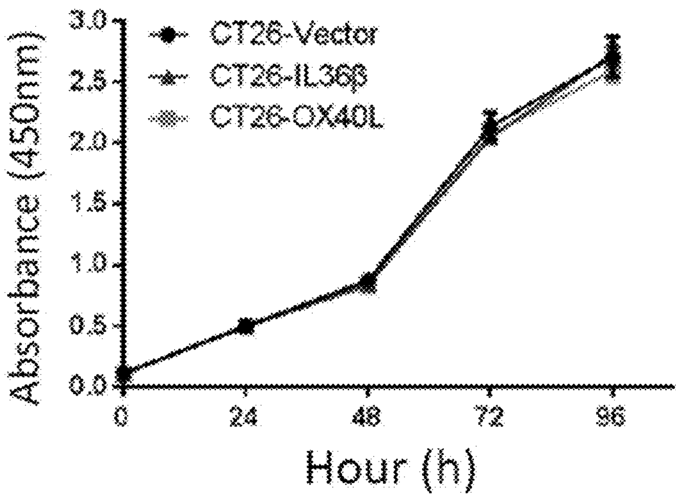
Figure 3D:
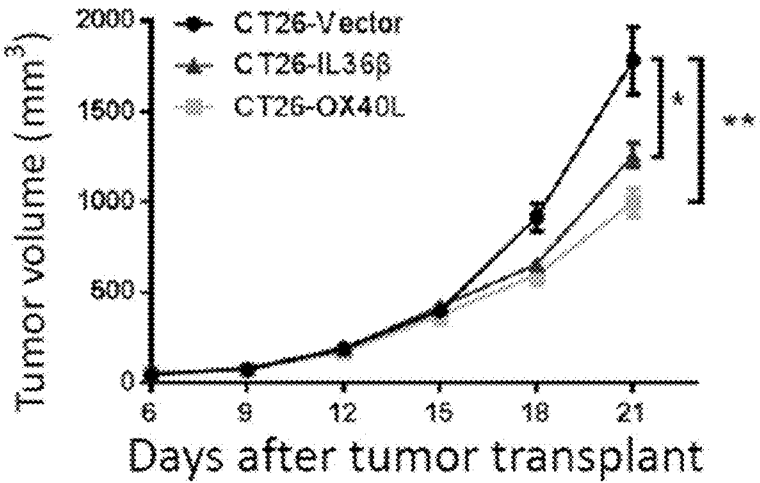

In order to search for immunostimulatory therapeutic molecules with high efficacy, chemokines and cytokines with potential anti-tumor function were selected, and genes were cloned into lentivirus vectors to package lentivirus carrying these genes. The CT26 colorectal cancer cell line transduced with these lentivirus containing genes or blank controls were used for subcutaneous xenograft to test the anti-tumor effect of these molecules. After overexpression of chemokine CCL3 and CXCL9 with potential anti-tumor effect in CT26 (FIG. 2A), the proliferation of cells in vitro was not affected (FIG. 2B), while the growth of subcutaneous xenograft in vivo was significantly inhibited (FIG. 2C), indicating that these chemokines may inhibit tumor growth through the immune system in vivo. Among them, CXCL9 has the most significant anti-tumor effect. The detection of the composition of immune cells in tumors via flow cytometry reveals that CXCL9 can indeed increase the infiltration of anti-tumor immune cells such as CD8, CD4 and NK (FIG. 2D).

In CT26 cells overexpressing the two immunostimulatory cytokines IL-36β and OX40L, it was also found out that the overexpression of these two cytokines does not influence tumor cell proliferation in vitro, but shows a significant suppressive effect on subcutaneous xenograft, suggesting that their anti-tumor functions may depend on the immune system in vivo. Among them, OX40L exhibits a higher anti-tumor effect.

Figure 4A:
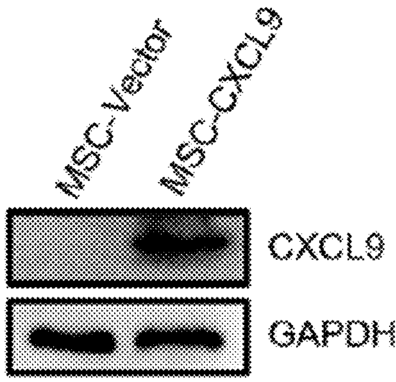
FIG. 4A to FIG. 4D show the identification of CXCL9 and OX40L overexpression in mesenchymal stem cells.
Figure 4B:
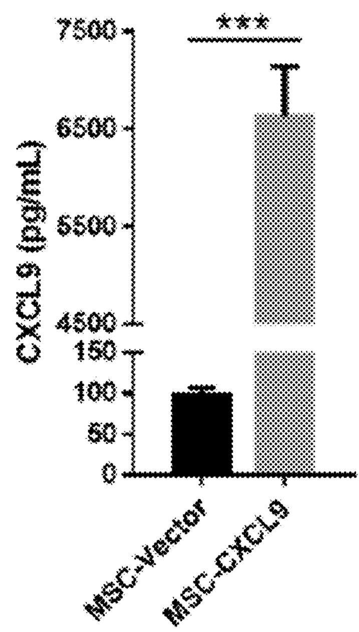
Figure 4C:
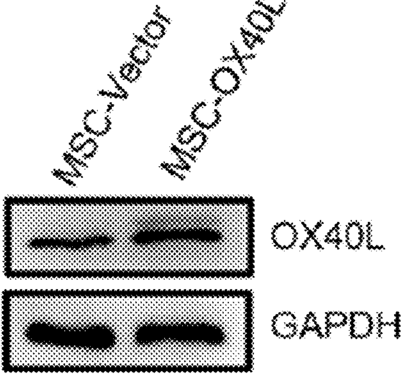
Figure 4D:
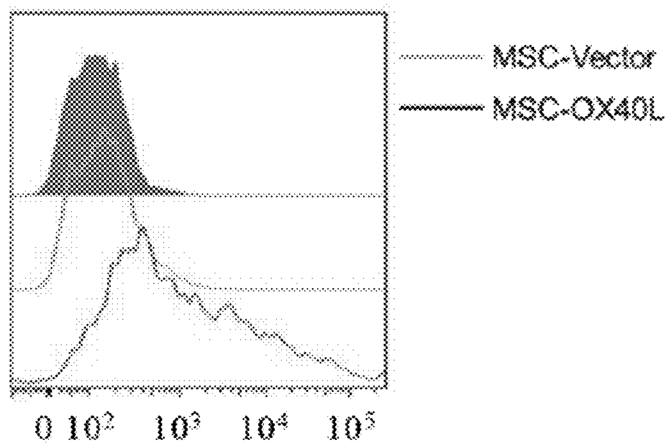
Figure 5A:
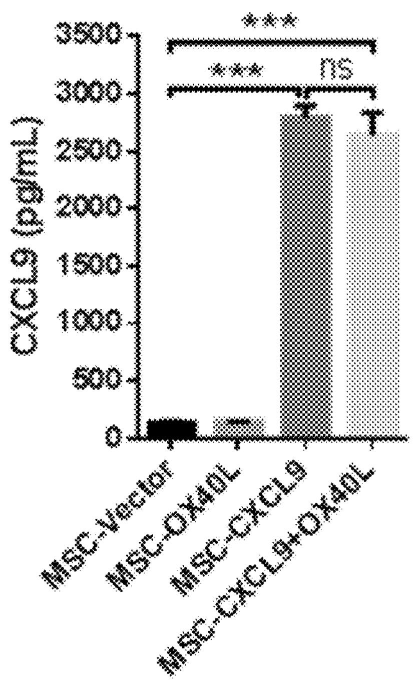
FIG. 5A to FIG. 5D show that mesenchymal stem cells overexpressing CXCL9 and OX40L suppress the growth of subcutaneous xenograft.
Figure 5B:
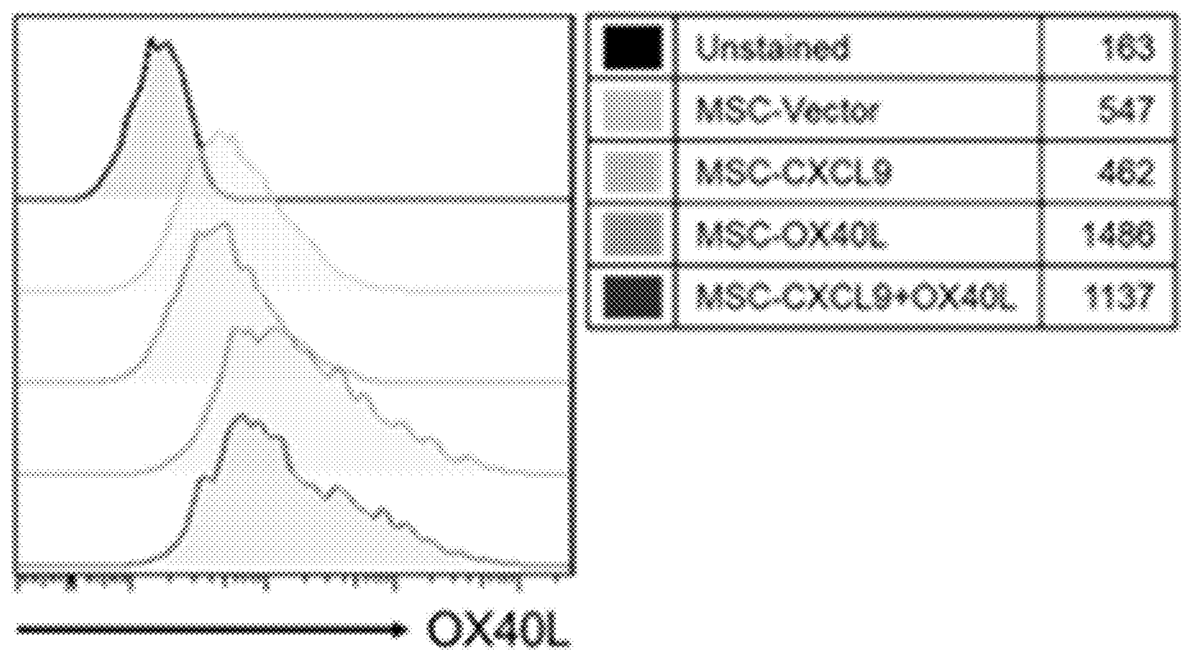
Figure 5C:
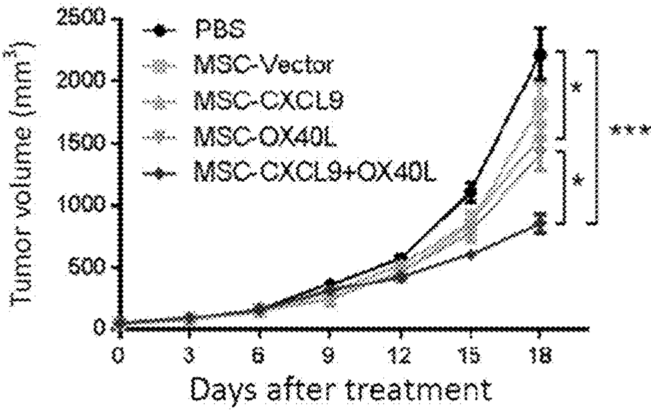
Figure 5D:
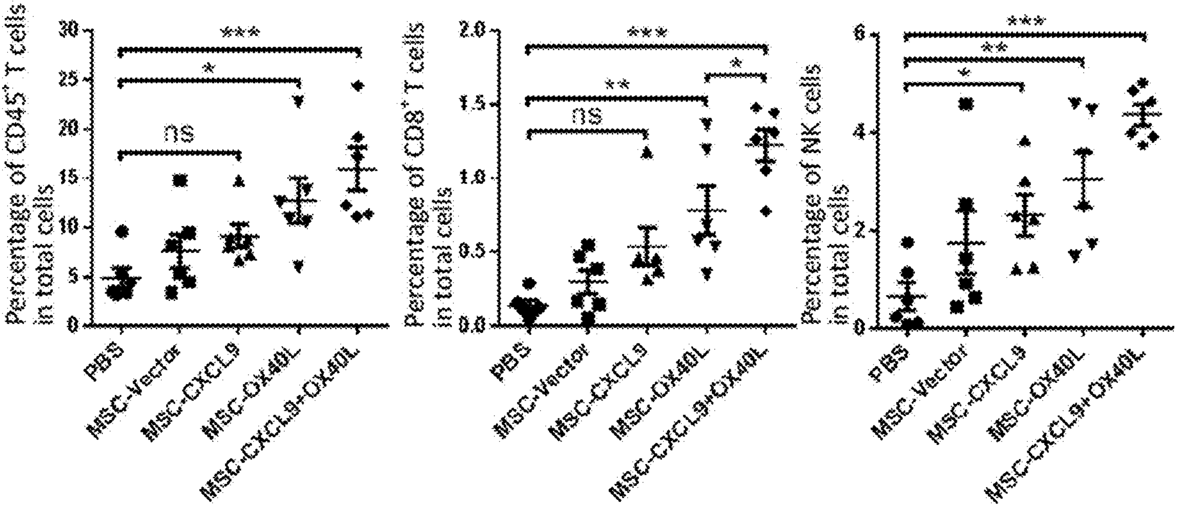
Figures 6A, 6B:
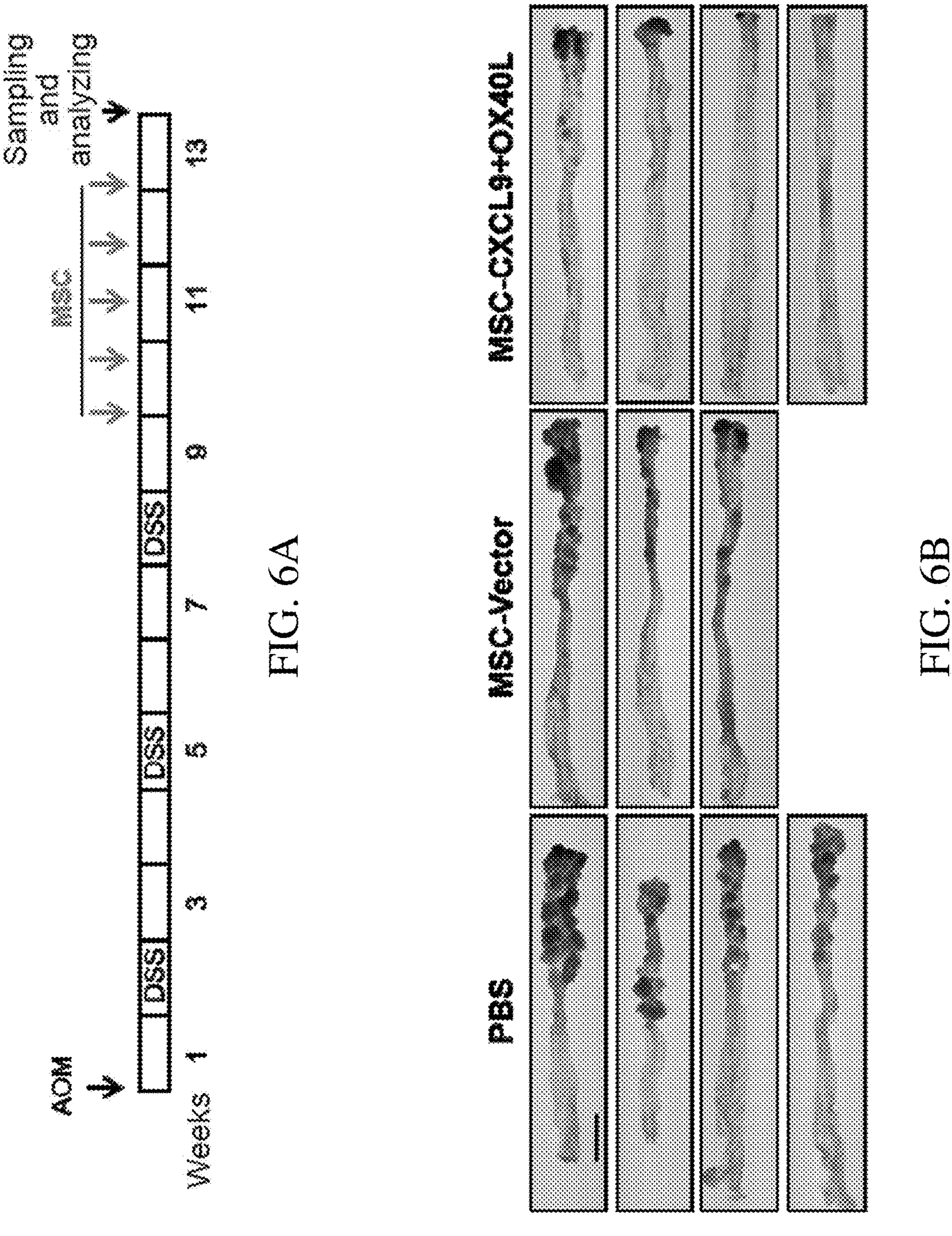
FIG. 6A to FIG. 6D show that mesenchymal stem cells overexpressing CXCL9 and OX40L suppress the AOM/DSS-induced colorectal cancer.
Figure 6C:
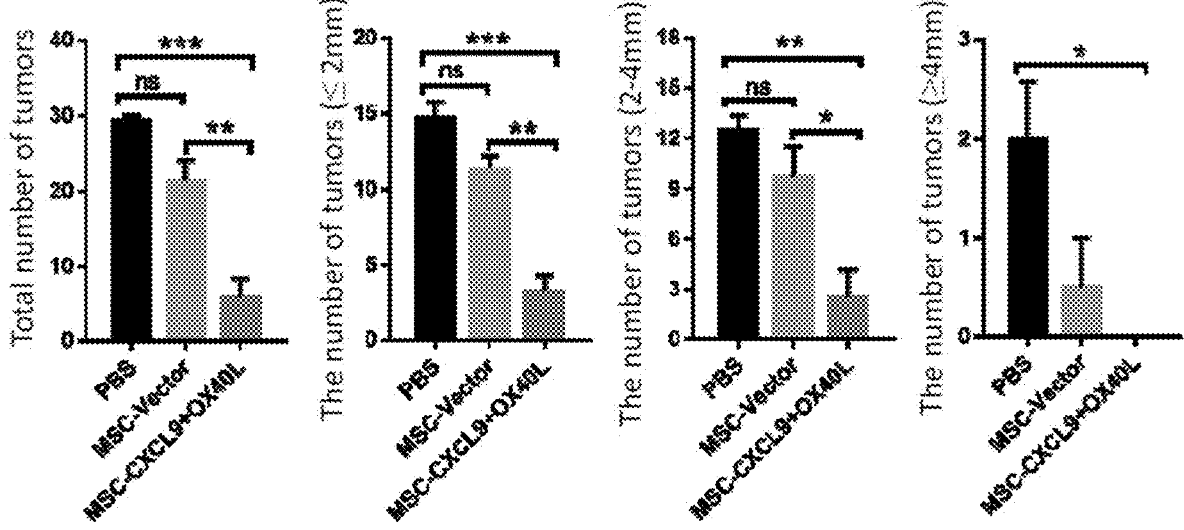
Figure 6D:
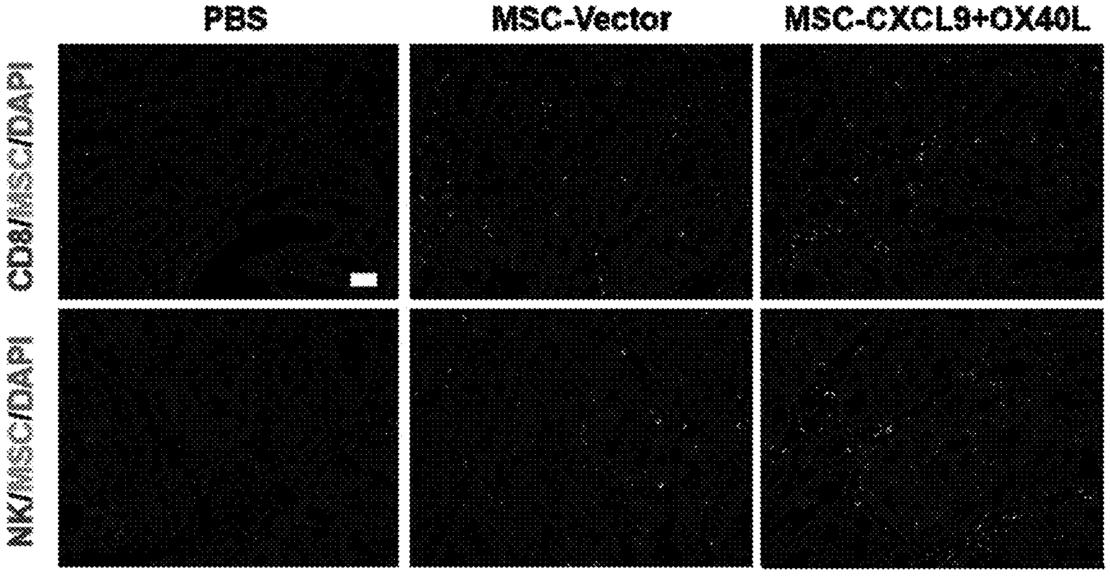

Example 3 Anti-Tumor Efficacy of Mesenchymal Stem Cells Overexpressing Chemokine CXCL9 and Cytokine OX40L Adipose mesenchymal stem cell system overexpressing CXCL9 and OX40L was established using lentivirus infection. The successful expression and secretion of CXCL9 were identified via Western blotting and ELISA (FIG. 4A& FIG. 4B), and the successful expression of OX40L on the cell membrane was confirmed via Western blotting and flow cytometry (FIG. 4C& FIG. 4D). After that, MSCs that simultaneously overexpress CXCL9 and OX40L were constructed (FIG. 5A& FIG. 5B). In the CT26 subcutaneous xenograft models, mice were injected with $5\times10^5$ mesenchymal stem cells or PBS each time through tail vein. After a total treatment for three times, each with a gap of four days, mesenchymal stem cells simultaneously containing CXCL9 and OX40L showed the strongest anti-tumor effect (FIG. 5C). It was found via flow cytometry that the proportion of lymphocytes, especially the anti-tumor CD8 T cells and NK cells, increased significantly in tumor (FIG. 5D), indicating that the therapy effectively activated the anti-tumor immune response. In order to further explore the efficacy of mesenchymal stem cell immunotherapy system, AOM/DSS was used to induce the model of inflammation-induced colorectal cancer in situ. From the last week of the third DSS treatment cycle, mice were treated for 4 weeks and a total of 5 times (FIG. 6A). PBS or $5\times10^5$ mesenchymal stem cells were injected each time through the tail vein. The mesenchymal stem cells containing CXCL9 and OX40L significantly reduce colorectal tumors in mice (FIG. 6B& FIG. 6C). Immunofluorescence staining showed that the infiltration of anti-tumor CD8 T cells and NK cells increased significantly (FIG. 6D), which is consistent with the results observed in the xenograft models.

Figure 7A:
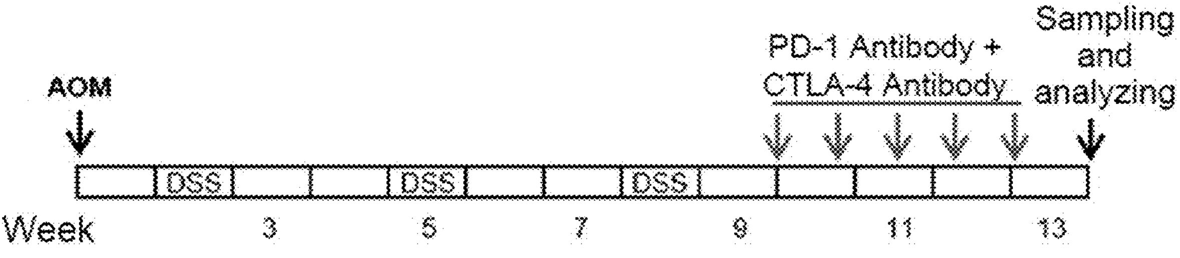
FIG. 7A to FIG. 7B show that the combination therapy of PD-1 and CTLA-4 antibody has no significant therapeutic efficacy for AOM/DSS-induced colorectal cancer.
Figure 7B:
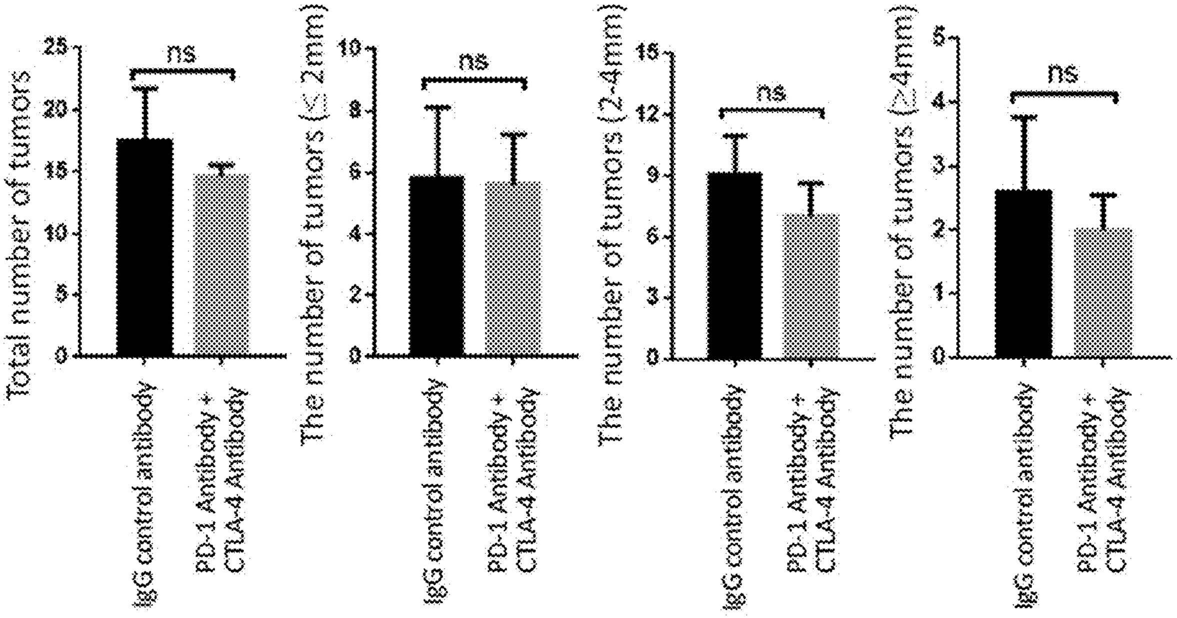

In contrast, PD-1 antibody (200 μg/mouse) and CTLA-4 (100 μg/mouse) were used in combination to treat mice of AOM/DSS-induced model of colorectal carcinoma in situ (FIG. 7A), and there was no significant change in tumor growth (FIG. 7B).

All the above results show that adipose mesenchymal stem cells overexpressing CXCL9 and OX40L show extremely significant therapeutic effects in models of mice subcutaneous xenograft and inflammation-induced colorectal carcinoma in situ. Mesenchymal stem cells simultaneously containing CXCL9 and OX40L express CXCL9 and OX40L, which have a synergistic effect, and the anti-tumor effect is significantly better than that of mesenchymal stem cells expressing CXCL9 or OX40L alone. In addition, the effect of mesenchymal stem cell therapy in the inflammation-induced colorectal carcinoma in situ model is significantly better than that of immunocheckpoint blocking therapy.

Figure 8A:
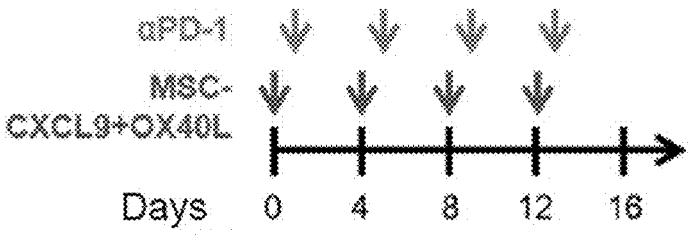
FIG. 8A to FIG. 8B show that mesenchymal stem cells overexpressing CXCL9 and OX40L promote the efficacy of PD-1 blocking therapy.

Example 4 PD-1 Blocking Therapy Efficacy is Increased by Mesenchymal Stem Cells Overexpressing Chemokine CXCL9 and Cytokine OX40L In the CT26 subcutaneous xenograft mouse models, mice were injected with mesenchymal stem cells (MSC) overexpressing CXCL9 and OX40L, PD-1 blocking antibodies (αPD-1) or both, for four times (FIG. 8A).

Figure 8B:
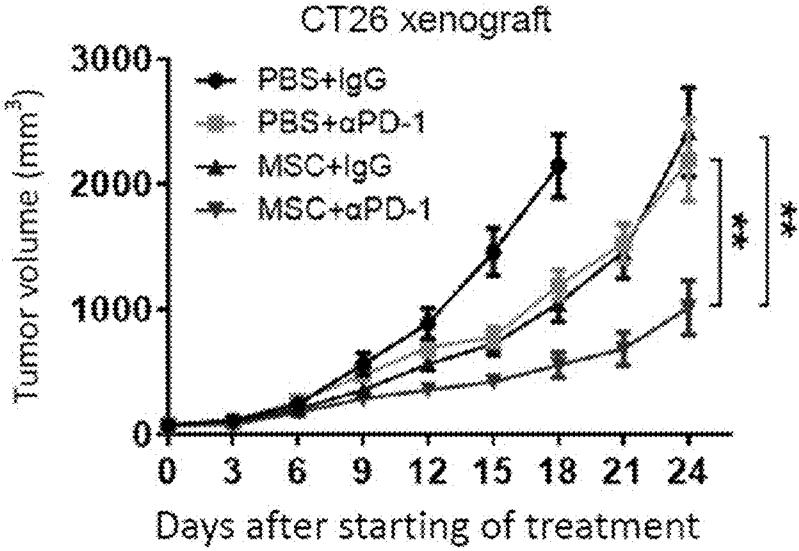

The results are shown in FIG. 8B. MSC and αPD-1 alone can significantly inhibit tumor growth, while combination therapy of MSC and αPD-1 is more effective in inhibiting tumor growth than two independent therapies, indicating that MSC therapy has obvious enhancement effect on PD-1 blocking therapy.

Figures 9A, 9B, 9C:
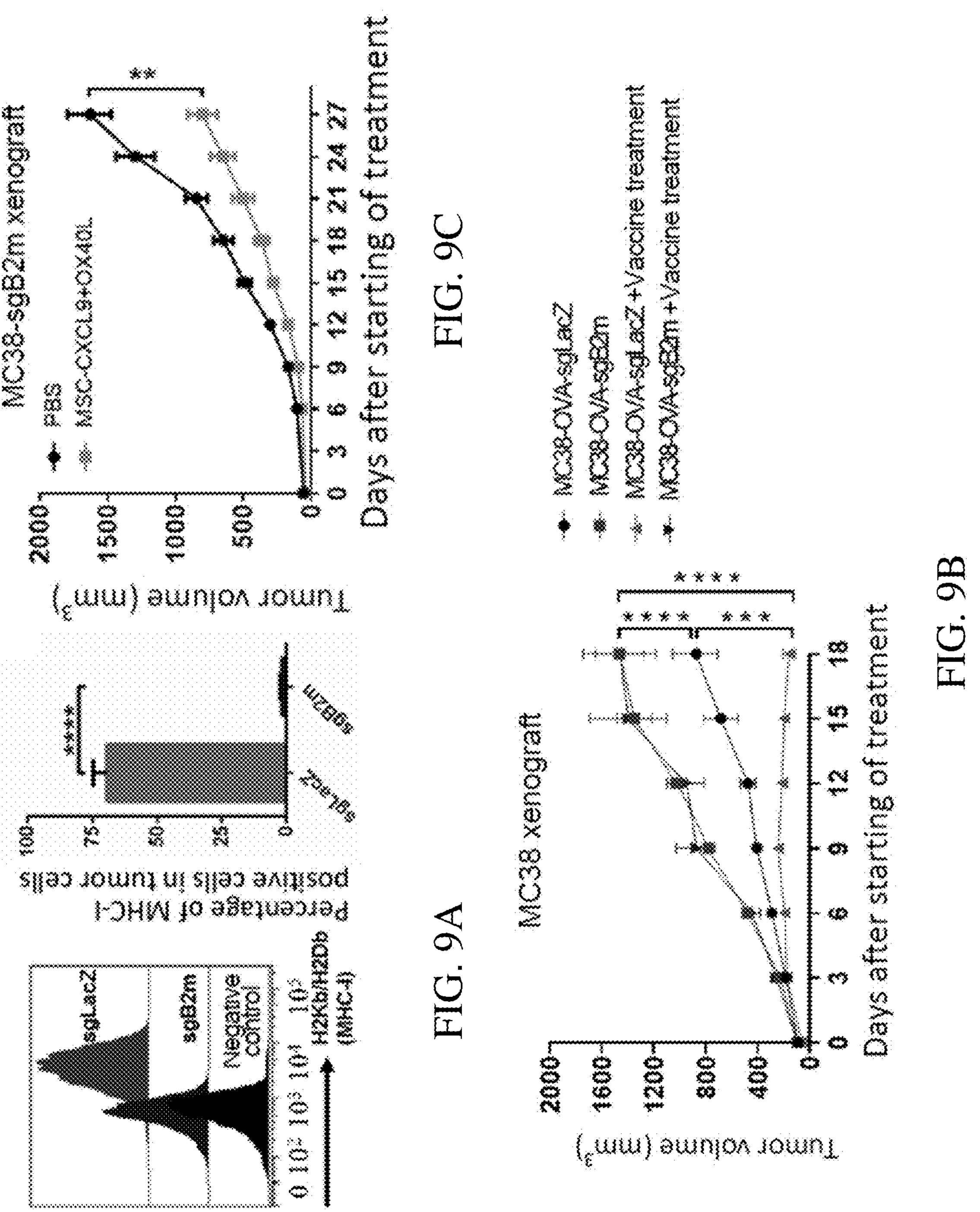
FIG. 9A to FIG. 9C show that mesenchymal stem cells overexpressing CXCL9 and OX40L suppress the growth of MHC-I-deficient tumors with immune evasive properties.

Example 5 Inhibiting Effect of Mesenchymal Stem Cells Overexpressing Chemokine CXCL9 and Cytokine OX40L on MHC-I-Deficient Tumors A MHC-I-deficient tumor model was successfully constructed by knocking out the B2m gene (sgB2m) in MC38 using CRISPR (FIG. 9A). On this basis, OVA gene was overexpressed to make tumor cells express specific OVA antigen. Compared with the control sgLacZ, the MHC-I-deficient MC38-sgBm grew faster and was not sensitive to OVA peptide vaccine treatment (FIG. 9B). However, mesenchymal stem cells overexpressing CXCL9 and OX40L can still significantly inhibit the growth of MHC-I-deficient MC38-sgBm tumors (FIG. 9C). It show that mesenchymal stem cell therapy has greater advantages than tumor vaccine for MHC-I-deficiency tumor.

Figure 10A:
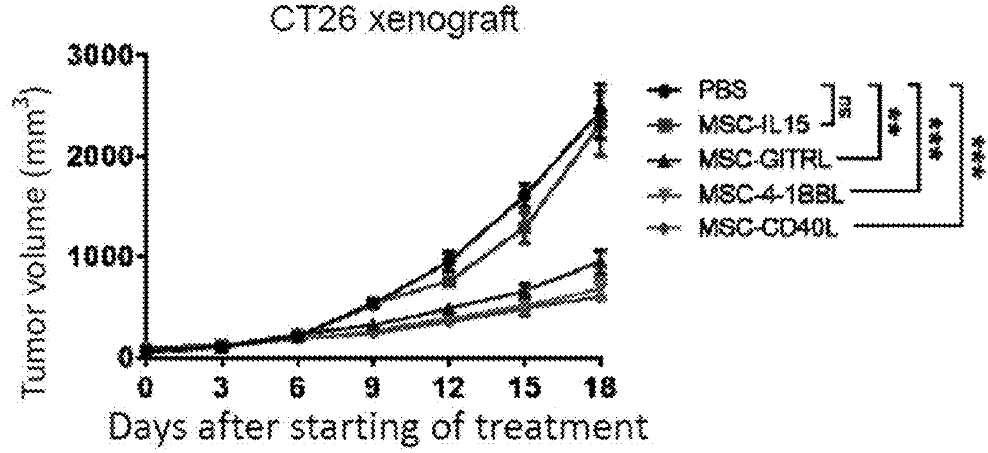
FIG. 10A to FIG. 10B show the therapeutic efficacy of mesenchymal stem cells (MSCs) overexpressing immunostimulatory factors/cytokines or chemokines. Each mouse received $5\times10^5$ mesenchymal stem cells overexpressing one of the factors every three days, for a total of six treatments.
Figure 10B:
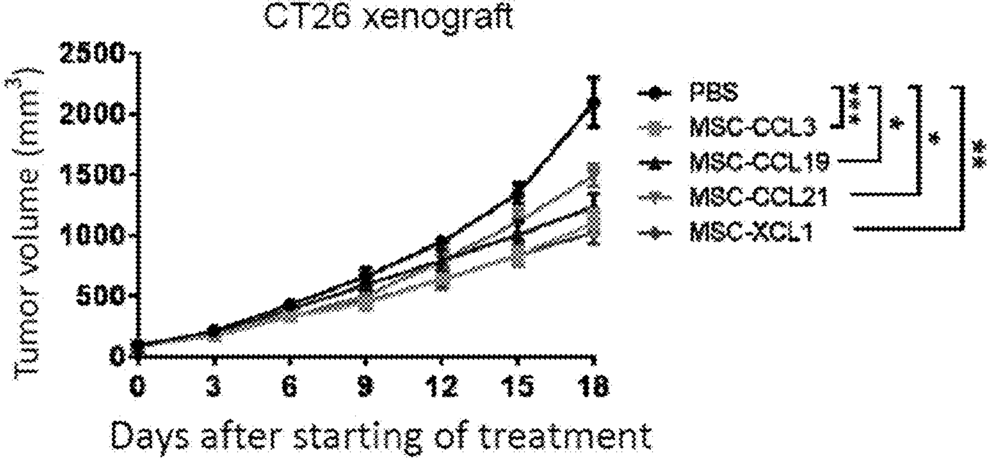

Example 6 Anti-Tumor Efficacy of Mesenchymal Stem Cells Overexpressing Other Chemokine or Cytokine In the CT26 xenograft model, mice were injected with mesenchymal stem cells expressing different cytokines or chemokines ($5\times10^5$/mouse/time) or PBS through the tail vein for six times. Mesenchymal stem cells overexpressing IL-15 does not show obvious anti-tumor effect, while mesenchymal stem cells overexpressing GITRL, 4-1BBL, CD40L shows high anti-tumor effect (FIG. 10A). Similarly, overexpression of several other chemokines CCL3, CCL19, CCL21 and XCL1 show significant anti-tumor effects (FIG. 10B).

Discussion

Immunotherapy has revolutionized the treatment of cancer. Although some cytokines and immune checkpoint blockers have shown significant efficacy in the clinical treatment of tumors, systemic use of these drugs will activate the immune system nonspecifically and affect most organs. In order to solve the side effects of systemic drug delivery, mesenchymal stem cells were selected as drug carriers. The research results show that adipose mesenchymal stem cells can actively migrate to the tumor site and are not enriched in organs such as liver, spleen and kidney, which fully supports the specificity and safety of mesenchymal stem cells as a carrier for tumor treatment drugs, and provides an effective means for local activation of immune responses in tumor to avoid systemic side effects.

The infiltration of T cells and NK cells in tumors is a key determinant of the efficacy of immunotherapy for solid tumors. Tumor can limit the infiltration of lymphocytes through different mechanisms. Tumors with more T cell infiltration usually highly express chemokines that can attract T cells, including CCL3, CCL4 and CXCL10. The present invention has unexpectedly discovered that using mesenchymal stem cells as a carrier to express and deliver CXCL9 to the tumor site to attract anti-tumor lymphocytes showed a stronger ability to attract T cells and NK cells, and solves the problem that lymphocytes are difficult to enter solid tumors. In addition, carrying OX40L in the mesenchymal stem cell system can also activate T cells and NK cells more efficiently. The activating antibody of OX40 receptor has entered the clinical stage (ClinicalTrials.gov), but the potential problem is the side effect of systemic medication. OX40L, the ligand of OX40, is a membrane protein. When expressed in mesenchymal stem cells, it can be transported to the tumor site and will not be secreted and transferred to other sites like secreted cytokines, reducing the diffusion caused by secretion, and can activate existing or newly migrated lymphocytes at the tumor site. The present invention also unexpectedly found that adipose mesenchymal stem cells overexpressing CXCL9 and OX40L showed extremely significant therapeutic effects in mouse subcutaneous xenograft and inflammation-induced colorectal carcinoma in situ models.

In general, the adipose mesenchymal stem cell therapy system established in the present invention that overexpresses chemokine CXCL9 and cytokine OX40L has the characteristic of specifically targeting tumor sites, and can attract and activate T cells and NK cells to achieve ideal anti-tumor effect. Compared with most immunotherapies, this therapy does not depend on the existence of tumor infiltrating lymphocytes, and is also applicable to the treatment of tumors with very low or resistance of lymphocyte infiltration in clinical practice. Adipose or umbilical cord mesenchymal stem cells are easy to extract and culture, and can be used for individualized treatment. Its low immunogenicity also makes the allogeneic application feasible. Therefore, the established immunotherapy based on mesenchymal stem cells has high clinical transformation value.

All documents mentioned in the present invention are incorporated by reference herein as if each document were incorporated separately by reference. Furthermore, it should be understood that after reading the foregoing teachings of the invention, various changes or modifications may be made to the invention by those skilled in the art and that these equivalents are equally within the scope of the claims appended to this application.

The invention claimed is:

1. A mesenchymal stem cell expressing the following immunostimulatory factors:

(1) CXCL9 and GITRL;

(2) CXCL9, 4-1BBL and GITRL; or (3) CXCL9, GITRL and CD40L.

2. The mesenchymal stem cell according to claim 1, wherein the immunostimulatory factors are CXCL9 and GITRL.

3. The mesenchymal stem cell according to claim 1, wherein the mesenchymal stem cell comprises: an adipose mesenchymal stem cell, an umbilical cord mesenchymal stem cell, or a combination thereof.

4. A preparation comprising the mesenchymal stem cell according to claim 1, and a pharmaceutically acceptable carrier, diluent or excipient.

5. A medicine kit comprising:

(1) a first container, and the mesenchymal stem cell according to claim 1 contained therein; and (2) a second container, and an antitumor immunotherapy agent contained therein.

6. The medicine kit according to claim 5, wherein the antitumor immunotherapy agent is an immune checkpoint antibody.

7. The mesenchymal stem cell according to claim 1, wherein the mesenchymal stem cell is ex vivo.

8. The mesenchymal stem cell according to claim 1, wherein the mesenchymal stem cell is autologous or allogeneic.

9. The mesenchymal stem cell according to claim 1, wherein the immunostimulatory factors are CXCL9, 4-1BBL and GITRL.

10. The mesenchymal stem cell according to claim 1, wherein the immunostimulatory factors are CXCL9, GITRL and CD40L.

* * * * *